(12) United States Patent
Schwartz et al.

(10) Patent No.: US 10,315,016 B2
(45) Date of Patent: Jun. 11, 2019

(54) SYSTEM AND METHODS FOR TREATING MVO

(71) Applicant: CorFlow Therapeutics AG, Baar (CH)

(72) Inventors: Robert S. Schwartz, Inver Grove Heights, MN (US); Martin T. Rothman, Santa Rosa, CA (US); Jon H. Hoem, Oberägeri (CH)

(73) Assignee: CorFlow Therapeutics AG, Baar (CH)

( * ) Notice: Subject to any disclaimer, the term of this patent is extended or adjusted under 35 U.S.C. 154(b) by 53 days.

(21) Appl. No.: 15/398,470

(22) Filed: Jan. 4, 2017

(65) Prior Publication Data

US 2017/0189654 A1   Jul. 6, 2017

Related U.S. Application Data

(60) Provisional application No. 62/379,074, filed on Aug. 24, 2016, provisional application No. 62/358,433, (Continued)

(51) Int. Cl.

| | |
|---|---|
| *A61M 25/10* | (2013.01) |
| *A61M 5/145* | (2006.01) |
| *A61M 5/172* | (2006.01) |
| *A61B 17/22* | (2006.01) |
| *A61M 5/142* | (2006.01) |

(Continued)

(52) U.S. Cl.
CPC ......... *A61M 25/1011* (2013.01); *A61B 17/22* (2013.01); *A61M 5/142* (2013.01); *A61M 5/1452* (2013.01); *A61M 5/1723* (2013.01); *A61B 17/32037* (2013.01); *A61B 2017/22054* (2013.01); *A61B 2017/22067* (2013.01); *A61B 2017/22071* (2013.01); *A61B 2017/22084* (2013.01); *A61B 2090/064* (2016.02); *A61M 2005/14506* (2013.01); *A61M 2025/0002* (2013.01); *A61M 2205/502* (2013.01); *A61M 2205/507* (2013.01); *A61M 2230/04* (2013.01); *A61M 2230/204* (2013.01); *A61M 2230/50* (2013.01)

(58) Field of Classification Search
CPC .............. A61B 17/22; A61B 17/32037; A61B 2017/22054; A61B 2017/22067; A61B 2017/22071; A61B 2017/22084; A61B 2090/064; A61M 2005/14506; A61M 2025/0002; A61M 2230/04; A61M 2230/204; A61M 2230/50; A61M 25/1011; A61M 5/1452; A61M 5/1723
See application file for complete search history.

(56) References Cited

U.S. PATENT DOCUMENTS

| | | |
|---|---|---|
| 4,689,041 A | 8/1987 | Corday et al. |
| 6,423,032 B2 | 7/2002 | Parodi |

(Continued)

OTHER PUBLICATIONS

WIPO, U.S. International Search Authority, International Search Report and Written Opinion dated Mar. 17, 2017 in International Patent Application No. PCT/US2017/012181, 16 pages.

*Primary Examiner* — Imani N Hayman
(74) *Attorney, Agent, or Firm* — Inskeep IP Group, Inc.

(57) ABSTRACT

Microvascular obstruction is treated by introducing injectate into blood vessels affected by microvascular obstruction at precise flow rates, while blocking retrograde flow, such that the natural pumping of the heart aids in forcing the injectate into the affected microvessels. Monitoring pressure distal of an occlusion balloon is used to determine treatment effectiveness and heart health.

23 Claims, 17 Drawing Sheets

Related U.S. Application Data filed on Jul. 5, 2016, provisional application No. 62/320,230, filed on Apr. 8, 2016, provisional application No. 62/274,744, filed on Jan. 4, 2016.

(51) Int. Cl.
    *A61M 25/00*    (2006.01)
    *A61B 17/3203*  (2006.01)
    *A61B 90/00*    (2016.01)

(56) References Cited

U.S. PATENT DOCUMENTS

| 8,876,850 B1 | 11/2014 | Vollmers et al. |
| 9,174,020 B2 | 11/2015 | Allen et al. |
| 9,205,226 B2 | 12/2015 | Allen |
| 9,550,046 B1 | 1/2017 | Allen et al. |
| 9,844,383 B2 | 12/2017 | Allen |
| 2004/0260333 A1 | 12/2004 | Dubrul et al. |
| 2010/0168649 A1 | 7/2010 | Schwartz et al. |

SYSTEM AND METHODS FOR TREATING MVO

RELATED APPLICATIONS

This application claims priority to Provisional Patent Application Ser. No. 62/274,744, filed Jan. 4, 2016, entitled Method and Device for Alleviating Micro-Vascular Obstruction, Thrombus, or Platelet Obstruction in the Coronary Arteries, Heart or Other Tissues, and claims benefit of and priority to U.S. Provisional Application Ser. No. 62/320,230 filed Apr. 8, 2016 entitled Myocardial Pump, and claims benefit of and priority to U.S. Provisional Application Ser. No. 62/358,433 filed Jul. 5, 2016 entitled Myocardial Pump and Method, and claims benefit of and priority to U.S. Provisional Application Ser. No. 62/379,074 filed Aug. 24, 2016 entitled Myocardial Pump and Method, all of which are hereby incorporated herein by reference in their entireties.

FIELD OF THE INVENTION

Methods and devices for the diagnosis and treatment of microvascular obstruction (MVO) and other diseases of the microvasculature. More particularly, non-limiting embodiments include novel devices and methods to successfully diagnose, restore patency, open and preserve flow, and limit reperfusion injury in organs and cases with microvascular obstruction. No methods are available to detect and measure or treat MVO in real time during scenarios such as invasive angiographic/therapeutic procedures. Such procedures include therapy for organ systems including the heart (acute myocardial infarction), brain (stroke (CVA), bowel ischemia/infarction, pulmonary emboli/infarction, critical limb ischemia/infarction, renal ischemia/infarction, and others. Using methods of the invention, a system comprising specialized infusion and sensing catheter, diagnostic agents, therapeutic agents, and control console with specialized algorithms can both diagnose and treat MVO by eliminating the microvascular clot and debris causing the obstruction. The techniques involve a combination of novel devices, methods, and software to diagnose and treat MVO. This will permit operation in real-time with real-time operator feedback for diagnostic and therapeutic decision making, and so create a system feasible for interventional procedures.

BACKGROUND OF THE INVENTION

Heart attack or STEMI ('STEMI' defined as acute ECG ST segment myocardial infarction) is caused by sudden occlusion of an epicardial coronary artery, typically fibrin and platelet rich clot, with associated and embolic plaque and debris. Electrocardiographic signs of acute transmural myocardial infarction (heart attack) are ECG tracings with ST segment elevation (STEMI). ST segment elevation is a hallmark of severe coronary artery narrowing, often with occlusion causing ongoing ischemic myocardial injury with cell death. Large vessel occlusion is often associated with small vessel occlusion (termed Microvascular occlusion or MVO) by clot and embolic debris, also a serious problem since the heart muscle is deprived of blood, oxygen, and critical nutrients necessary to sustain cell life.

Interventional cardiology is very proficient at opening severely narrowed or occluded epicardial coronary arteries in the cardiac catheterization laboratory using catheters, guide wires, balloons, and stents. However, microvascular obstruction cannot be diagnosed in the Cath lab, and more importantly MVO cannot be treated even if/when it could be accurately diagnosed.

Heart muscle salvage (saving muscle from death due to lack of blood and oxygen) is a critical concern to ensure good long-term outcomes in patients suffering STEMI. A key component of good long-term outcome involves minimizing the time between coronary artery occlusion (at home or outside the hospital) and opening the occluded artery in the cath lab. Interventional Cardiologists can reduce artery occlusion time by implementing streamlined and efficient emergency medical systems whose goal is to have STEMI patients arrive in catheterization laboratory as soon as possible, avoiding long term STEMI complications. Complications resulting from STEMI and MVO include, systolic and diastolic heart failure, arrhythmias, aneurysms, ventricular rupture and multiple other serious complications. These complications can markedly shorten life and impose severe limitations on quality of life.

Modern interventional therapy for acute myocardial infarction has matured over time with impressive clinical results. Heart attack/STEMI death rates at 30 days have dropped from more than 30% to less than 5%, achieved by reperfusing the heart with blood as soon as possible during coronary arterial occlusion. This goal is accomplished by streamlining clinical care systems to open coronary arteries in the catheterization lab as rapidly as possible after heart attack onset. Emergency procedures including stenting and balloon angioplasty are undisputed as necessary for improving early and late clinical results of acute heart attack therapy.

However, substantial challenges remain for treating STEMI patients and reducing long term complications. These problems include heart failure (poor cardiac function and cardiac enlargement), cardiac/ventricular rupture, persistent ischemic chest pain/angina, left ventricular aneurysm and clot, and malignant arrhythmias.

Late Heart failure complicates 25-50% of acute STEMI, caused by poor Left Ventricular function and damaged myocardium. Heart failure is worsened as the heart remodels in shape and size, and loses function. Nearly half of all new heart failure in patients under 75 years is linked to STEMI.

Many years investigating STEMI therapy show that opening the epicardial/large coronary artery is insufficient to salvage heart muscle and optimize long term patient outcome. The most common reason for poor late results after heart attack is microvascular obstruction (MVO). MVO is occlusion or severe flow limitation in the internal cardiac microvessels, typically by clot. These microvessels are impervious to stenting and conventional thrombolytic therapy. Thus, despite a widely patent epicardial coronary artery, residual MVO obstructs blood flow into the heart causing cell ischemia death from severe heart muscle damage.

MVO thus remains a critical frontier in cardiology. Cardiac microvessels comprise small arteries, arterioles, capillaries and venules which are frequently filled with clot and debris (platelets, fibrin, embolic plaque material) during STEMI. Too often, obstructed microvessels (MVO) do not resolve even after stent placement, and have serious long-term negative prognostic implications.

MVO is very common in STEMI patients, even though stenting and balloon angioplasty are successful at opening epicardial coronary arteries. MVO occurs in more than half of all STEMI patients, even with good blood flow through open epicardial arteries and newly placed stents.

MVO extent is key to the severity of myocardial damage and patient outcome. MVO is best imaged via cardiac MRI which measures MVO location, extent and severity. MRI, however, cannot be performed emergently or during a cardiac catheterization procedure since it requires patients to be in a separate imaging area and within a separate scanner. FIG. 13A shows regions of profound MVO at the myocardial infarct core, having very dark muscle with no contrast flowing into the cardiac segment. FIG. 13B is a repeat scan 6 months later in the same patient, and shows dense heart scarring (white line of tissue replacing the black region) that resulted from the MVO.

Important features of MVO may be summarized by the following:
1. MVO in STEMI is the principal cause of major complications early and late after heart attack.
2. Angiographic "no-reflow" or "low-reflow" is caused by MVO and is due to obstructed microvessels within the heart. MVO is fluoroscopically characterized by very slow X-ray contrast filling the epicardial coronary arteries as visualized during coronary treatment in the catheterization laboratory.
3. MVO causes myocardial cell injury and death from prolonged ischemia/lack of oxygen, blood, and key metabolic nutrients such as glucose. MVO microscopic analysis shows microvessels filled with platelet and fibrin clot, dead myocardial cells, inflammatory cells, myocyte cell death, and endothelial cell death along the obstructed intramyocardial capillaries.
4. MVO studied acutely shows cardiac arterioles and capillaries completely occluded by platelet and fibrin-rich thrombus, platelet-neutrophil aggregates, dying blood cells and embolic debris.
5. When MVO complicates acute STEMI/myocardial infarction, far greater heart/myocardial damage occurs, and poor ventricular function occurs early.
6. MVO is very common. It occurs in:
   a. 53% of all STEMI and NSTEMI regardless of epicardial flow
   b. 90% of Large Transmural STEMI
   c. 40% of MI with TIMI III (normal) X-ray visualized flow
   d. MVO is the single most potent prognostic marker of events after controlling for infarct size
7. Patients with microvascular obstruction have more late major adverse cardiovascular events (MACE) than those without MVO (45% versus 9%)
8. MVO is the best predictor of acute and chronic cardiovascular adverse outcomes.
9. MVO acutely becomes late fibrous scar and causes poor Cardiac function.

MVO cannot be diagnosed in a catheterization laboratory. Moreover, no effective therapies are available. Many possible prior therapies all proved essentially ineffective, and in some cases, dangerous.

Problems encountered with prior MVO therapy include rapid fluid bolus injection with drugs. This failure is best understood as fluids follow paths of least resistance. MVO-obstructed vessels have very slow flow, with very high hydraulic resistance. Direct drug bolus into coronary arteries has little effect against MVO because the injected agent enters only open and unobstructed microchannels, with little or none entering obstructed microvessels in STEMI. Studies suggest that only 1/1000 of a locally injected drug enters obstructed microvessels, most drug entering the open and unobstructed microvessels. Delivering high drug doses to occluded microchannels in this adverse ratio yields unacceptably high toxic systemic drug level because all injected drug eventually enters the systemic circulation. High systemic drug levels place patients at risk of dangerous systemic bleeding and other systemic complications including vessel dissection due to high flow infusion rates.

Solving MVO is a critical need for Cardiologists. Technology and methods to successfully and efficiently deliver therapeutic agents to MVO-obstructed microvessels of multiple organs (Heart, brain, bowel, extremities, liver, kidneys for example) are not available. Such therapy must be simple, efficient, safe, and easy to use in the catheterization lab. Such methods must deliver high dose therapeutic agents into occluded channels without causing toxic systemic concentrations, and to be available to treat the microvessel after flow restoration will permit a further goal of preventing or limiting reperfusion injury.

OBJECTS AND SUMMARY OF THE INVENTION

This application describes novel devices and methods for both diagnosing and treating MVO emergent in the Cath Lab. It allows monitoring treatment efficacy in real time during the therapeutic interventional procedure. The invention uses a compact computerized console and fluid pump with unique and specialized fluid infusion algorithms together with a unique catheter system having both diagnostic and therapeutic capabilities. MVO diagnosis can be made and treatment assessed in real time via flow controlled multi-agent (both therapeutic and diagnostic) infusion. The integrated system provides precise cardiac or other organ (brain, lung, kidney, limb, visceral organ and others) microcirculatory characterization in real-time to diagnose MVO and precisely guide therapy in real time.

Generally, the invention provides a catheter based device including a compliant balloon that safely and completely occludes antegrade flow in a large epicardial feeder vessel responsible for STEMI or other tissue infarct. Procedurally the invention involves placing the catheter in the large vessel proximal to an MVO-affected myocardial region. Balloon inflation completely obstructs antegrade artery flow, and within seconds a "waterfall pressure" (aka Coronary Artery Wedge Pressure) is measured. This is achieved via a distal pressure transducer (pressure guidewire or by pressure transducer integral to the distal end of the balloon or on a balloon catheter nose extension). The Waterfall pressure is a key physiologic parameter for assessing cardiac status, collateral vascular patency, propensity for malignant arrhythmias, myocardial ischemic status, and therapeutic progress. It is further described below.

Accurate Microvascular resistance is derived from pressure measurement distal to the occluding balloon at the same time as a known and precisely controlled flow is infused through distal balloon catheter ports. A regulated, precisely defined flow infusion by a specialized hydraulic pump fills the catheter after balloon inflation causing complete vessel occlusion just proximal to the infusion holes. Distal vessel and microvascular bed receive this flow and generates a filling pressure. The principal MVO diagnostic mechanism is that obstructed microvessels subjected to defined fluid flow generate back pressure with value directly proportional to the microvascular resistance. The filling pressure is measured via pressure sensor also distal to the occlusion balloon, permitting precise microvascular resistance calculation:

Microvascular Resistance=(measured distal Pressure)/(Known infusion Flow).

Slow flow occurs in normal, healthy cardiac microvasculature through the Starling Resistor effect as follows. Normal microchannels within cyclically contracting heart muscle undergo forced collapse during cardiac systole, as cardiac muscle develops high interstitial pressure. The cardiac microvasculature thus comprises multiple Starling Resistors. The Starling resistor effect is defined for elastic, fluid-filled collapsible tubes within a closed pressurized chamber. Fluid flow through the elastic tube is a highly nonlinear function of chamber pressure in which the elastic tube resides. As chamber pressure exceeds pressure in the collapsible tube (the Waterfall Pressure), the elastic tube collapses completely and prevents flow. If the therapeutic fluid is a drug intentionally infused at slow rates, drug flow entering the unobstructed capillaries is more closely equalized to the slow flow in the MVO obstructed capillaries. The improved flow match occurs as drug dwell time at capillary ostia is markedly prolonged, allowing greater drug volume (dose or mass) to enter the occluded microchannel. Slow drug infusion at low pressure is a unique method for deliberate microvascular resistance equalization in obstructed and unobstructed microchannels. Drug delivery to MVO channels is enhanced by slow infusion thus obtained as infusion pressure is at or near Waterfall pressure. If infused flow rates are low enough to drop pressure below Waterfall level, resistance from normal/patent vessels is increased.

The drug concentration-time integral is a key parameter for optimizing therapeutic entry into MVO channels. For example, a rapid drug bolus injection into the coronary artery causes the drug to selectively enter the normal, fast flowing and unobstructed microvasculature. The concentration-time integral is a very small number. A much-improved concentration-time integral can be achieved by filling the proximal circulation with drug, and by ceasing pump action completely with an inflated and obstructing proximal balloon. High-concentration drug in the completely stopped flow dwell at the ostia of capillaries, but is slowly driven into both MVO and unobstructed microcirculatory vessels via the Waterfall pressure. Additionally, the cyclic myocardial pump action further serves to draw drug into both MVO and normal capillaries due to physiologic suction facilitated by proximal balloon occlusion and cyclic capillary collapse-rebound opening.

The contracting heart muscle squeezes microvessels closed with each systolic beat. Because the epicardial artery is occluded by a catheter-balloon, a natural, antegrade pumping effect is created. This pump creates suction during diastole, enhancing drug entry into the occluded channel. During systole, the very high (balloon induced) proximal resistance combined with lower distal resistance forces antegrade flow and makes a natural antegrade fluid rectifier. Together, this system permits enhanced local drug dose over time. It thus avoids very high toxic systemic doses.

The Diagnostic component of the invention is created as the computer-controlled pump infuses drug or any suitable solution at a range of flow rates. Back pressure generated from these rates is directly proportional to microvascular resistance, so that therapeutic infusion simultaneously becomes a diagnostic infusion. Such a configuration permits simultaneous therapy and diagnostic efficacy assessment.

The invention provides methods for treating MVO involving one or more of the following steps: Navigating a catheter into a myocardial vessel supplying blood to occluded microvessels of the myocardium; blocking and occluding (temporarily) antegrade and retrograde blood flow around said catheter using a inflatable balloon or other device; introducing infusate through a lumen at controlled and known rates, of said catheter and out of distal ports; preventing retrograde flow into the coronary artery of the infusate. Instead it assists in forcing flow antegrade by natural myocardial systolic contractions serving to pump the drug infusate antegrade into and though the heart microvessels. This is an assist of physiologic pumping for bringing the infusate, including diagnostic fluid and drug(s), into and through the occluded or partly occluded myocardial microvessels. Useful coronary physiologic data results by monitoring flow and pressure parameters in the myocardial vessel near a distal end of the catheter during balloon occlusion. The Waterfall Pressure described above is such a physiologic parameter; and also assists by supplying positive pressure to the fluid, also facilitating antegrade flow. Measuring and analyzing pressure parameters is straightforward and such analysis determines the magnitude of obstruction by the occlusive microvascular clot and plaque debris.

In one aspect of the invention, the infusate is an infusate crystalloid (Ringer's Lactate) balanced electrolyte solutions with specific electrolytes and glucose, FFP (plasma or derivatives), and infusing other physiologic solutions. The infusate may also be oxygenated. The infusate may be whole blood obtained from the patient during the procedure or previously, as an 'autotransfusion'. The infusate may also be blood from another patient, whole blood, plasma, or any blood-derived product.

In another aspect of the invention, introducing infusate may involve a catheter and its lumen in a repeating inject-stop-hold pattern wherein the inject step indicates forcing infusate through the catheter.

In yet another aspect of the invention a therapeutic, time-dependent waveform or a waveform determined by sensed physiologic parameter (flow, pressure, resistance, heart rate) are synchronized to myocardial contraction, or to the physiologic parameters noted above and carefully followed.

In yet another aspect of the invention, two obstructing balloons are in place, with a catheter space between. The distance apart is variable, the purpose of which is to test microvascular resistance and microvascular function between the two occlusive balloons. The balloons are designed to straddle a region of a major coronary artery prior to inflation. During inflation, there is thus an isolated vessel segment. The catheter between the balloons has a set of infusion holes, and one or more pressure transducers. The infusion port has multiple small holes to inject both diagnostic and therapeutic fluid, identical to the remainder of this application. The pressure transducer measures microvascular effects on controlled and known flow, so that microvascular resistance is calculated from pressure and known flow. This configuration of infusion holes, isolating balloons (two or more), and pressure transducers permits measuring microvascular resistance over any segment of artery, and can thus be of value in determining where MVO or other microvascular dysfunction exists.

One embodiment of the invention pertains to a method for treating Microvascular Obstruction (MVO) comprising: navigating a catheter into a myocardial vessel supplying blood to a patient's myocardium with MVO; blocking antegrade and retrograde blood flow within the vessel around said catheter using a balloon; measuring a fluid pressure of the myocardial vessel occurring distal of the balloon; introducing infusate through a lumen of said catheter; allowing natural myocardial contraction and compression of the microvasculature to pump the infusate antegrade into occluded myocardial vessels and to promote mixing of the infusate with obstructing matter causing MVO; collecting data pertinent to pressure parameters in the myocardial vessel; analyzing the collected data to determine a change in microvascular resistance; said change resulting from said treating the MVO.

In one embodiment of this method, the temperature of the fluid in the myocardial vessel is also measured.

The method may include collecting data pertinent to temperature parameters in the myocardial vessel. In one embodiment of this method, the temperature of the fluid in the myocardial vessel is also measured.

In another embodiment of the invention, the obstructing balloon may contain a stent for delivery to a site of arterial compromise. This embodiment allows stent delivery followed by microvascular pressure assessment using a single balloon.

In another configuration, the catheter may contain an electronic identification mechanism such as an RF-ID chip or similar device. This may be used to identify the catheter type, flow configuration, flow resistance, permissible flow and pressure specifications and features, manufacture parameters, safety parameters, and the like.

In another configuration, the invention may be contained within a short, coupling catheter that connects the pump to a conventional stent delivery or other intravascular balloon. This short coupling catheter contains pressure sensing for flow infused into the conventional catheter. It also may have a specific, known infusion lumen diameter yielding a known hydraulic impedance. It may also have 2 or more pressure sensors spaced at a fixed distance apart yielding an known hydraulic impedance.

The infusion holes may be cut into the infusate exit lumen at an angle different from perpendicular to the catheter axis, permitting diffusion longitudinally down the arterial axis rather than perpendicular to the axis.

The method may be embodied such that introducing infusate through a lumen of the catheter comprises repeating an inject-stop-hold pattern until total elapsed occlusion time nears that of physiologic myocardial or organ injury due to ischemia.

The method may also be embodied such that introducing infusate through a lumen of the catheter comprises introducing infusate through an arterial or venous lumen at least one predetermined flow rate or rates. Additionally, this embodiment may further include varying the predetermined flow rate to match a waveform. This waveform may be selected from the group including steady, square, triangle, sine, step-function (ladder wave), and custom time dependence. One component of the flow injection may be to completely stop flow for a specified period of time, increasing the concentration-time of drug at the microvascular orifice/lumen.

One embodiment of a method of the invention includes analyzing the collected data comprises deriving a value Tau, where Tau is derived as a mono-exponential fit, $$P(t) = P_0 e^{-t/Tau}$$

In the exponential pressure decay, Tau is the time taken by the system for the pressure to drop to $1/e=0.37$, or when the pressure drops to 37% of its initial value. Tau can be measured using the invention by recording an initial pressure $P_0$, and determining the time point at which the pressure drops to $0.37*P_0$. Tau is that time value.

Another embodiment is a method of quantitating pressure change using a polynormial series, deriving coefficients according to standard polynomial time series expansion:

$$P(t) = \sum_{k=0}^{n} a_k * p^k$$

In yet another embodiment, the method may be embodied such that analyzing the collected data comprises quantifying the flow rate through the organ.

The method may further include determining a waterfall pressure, wherein the waterfall pressure is defined as the asymptotic value of the monoexponential Tau fit. The waterfall pressure may be used as a guide for infusion pressure.

The method may be embodied such that the step of blocking antegrade and retrograde blood flow within the vessel around a said catheter using a balloon comprises blocking the antegrade and retrograde blood flow within the vessel around said catheter using at least a first balloon and a second balloon spaced apart from the first balloon. Pressure may then be measured between the first and second balloons. This configuration creates a series of inter-balloon spaces, isolated from native blood flow when the balloons are inflated. Each interballoon space, after inflation, becomes an isolated zone for measuring segmental pressures, tau, and resistance/MVO. Varied combinations of balloon inflation (e.g. 1-2, 1-3, 2-3 etc.) will permit segmental resistance assessment without the need for moving the catheter. A guidewire lumen can be connected to the interspace regions to serve as a single pressure monitor. This configuration permits resistance measurement of small myocardial segments subtended by the space created between inflated balloons.

Another method of the invention pertains to reestablishing blood flow through occluded microvessels including the steps of navigating a catheter into a vessel supplying blood to the occluded vessels; blocking antegrade and retrograde blood flow around a distal end of said catheter; monitoring at least one of a pressure inside the catheter, and a pressure outside a distal end of the catheter; pumping infusate through a lumen of said catheter in a patterned response having a pattern that is selected based on at least one monitored pressure; preventing retrograde flow of the infusate around the catheter such that natural cardiac contractions at least partially aid in pumping the infusate antegrade into the occluded vessels; altering the pattern as the at least one monitored pressure changes; and analyzing data collected during the monitoring step to determine whether and to what extent blood flow has been reestablished.

This method may be embodied such that the patterned response comprises a repeating inject-stop-hold pattern. The inject portion of the inject-stop-hold pattern comprises injecting at defined rates. These defined rates may vary over time, according to the monitored pressure. The patterned response may match a waveform having amplitudes and phases derived from said at least one monitored pressure.

This method, like the aforementioned method, may be embodied such that analyzing data collected comprises deriving a value Tau, where Tau is derived as a mono-exponential fit of the equation $$P(t) = P_0 e^{-t/Tau}$$

The method may also be embodied such that analyzing data collected comprises quantifying the microvascular state and flow rate through the organ.

The method may also be embodied such that analyzing data collected comprises determining a waterfall pressure, wherein said waterfall pressure is defined as the asymptote of the monoexponential fit. This waterfall pressure may be used as a guide for infusion pressure of therapeutic or diagnostic agents.

Analyzing the data collected may also include determining an autoregulatory status of an organ's microvascular function, and assisting in diagnosing diseases of the microvasculature such as Syndrome X, Transplant microvasculopathy, pulmonary hypertension, renal vasculopathy. The data from microvascular resistance will also diagnose myocardial viability or scar, and can be used for ischemic stress testing when combined with common stress agents such a dobutamine, dopamine, or adenosine, and definition of myocardial diastolic dysfunction.

The invention also provides a system for treating myocardial MVO. The system may include a fluid pump assembly including: a pump; at least one fluid reservoir connected to the injector containing therapeutic or diagnostic injectates and associated with said pump such that operation of said pump forces injectate from said reservoir through said injector cartridges in an automated or manual selection; a catheter having a distal end and a proximal end connected to said injector reservoir arrays; an inflatable balloon near said distal end of said catheter; at least one pressure and temperature sensor located to measure at least one of a pressure and/or temperature value inside a distal end of the catheter, a pressure/temperature inside the catheter; and a pressure and a temperature value outside the catheter distal to the balloon; said pressure/temperature sensor associated with said fluid pump assembly such data acquired from said pressure/temperature is used for setting infusion parameters of said fluid pump assembly; wherein said pump is configured to pump said injectate at a flow rate based on said inputted pressure and temperature data.

One embodiment of the system also includes a user interface electronically associated with said pressure sensor, said user interface displaying a graph of calculated values over time based on said pressure data. The graph may be used for decision making regarding further therapy or diagnosis. The user interface may be configured such that it displays a waterfall pressure, wherein waterfall pressure is defined as the steady state arterial pressure distal to the balloon following balloon inflation and occlusion.

The system may be embodied such that said user interface displays tau, wherein tau is defined as the parameter which best characterizes exponential decay according to the equation $p(t)=P_0 e^{-t/TAU}$. The Tau parameter represents the time at which measured pressure decays by about 1/e or about 67% of it pressure immediately following balloon inflation.

The system may be embodied such that the user interface displays the distal pressure and/or temperature value, the flow infusion value and any derivate of these parameters such as the calculated vascular resistance (pressure divided by flow). The user interface may also display the real-time status of inflated occlusion balloon; inflated or deflated and the internal pressure in the balloon. The system may further be embodied such that the status of the occlusion balloon (deflated or inflated) automatically triggers the calculation of the Tau, the waterfall pressure or any other derived parameter of the measured pressure, flow, temperature or vascular resistance values.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
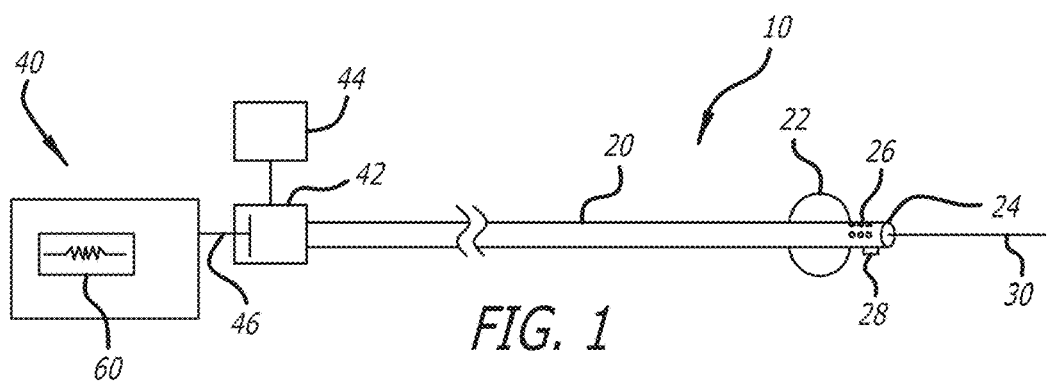
FIG. 1 is a diagram showing the general components of an embodiment of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring now to the figures, and first to FIG. 1, there is shown an embodiment of a system 10 of the invention. The system 10 generally includes a catheter 20 with an occlusion balloon 22 near a distal end 24 of the catheter 20. The occlusion balloon 22 may be spaced apart from the distal end 24 enough to provide space for components occurring in some embodiments of the system 10 such as side flow holes 26 and/or a distal pressure sensor 28.

At a proximal end of the catheter 20, there is an electronic fluid pump assembly 40. The electronic pump assembly 40 includes a hydraulic switch 42 for connecting one or multiple different injectate reservoirs 44 to a pump 46, such as a roller pump or plunger, to provide precisely controlled flow through the catheter 20. A distal end of the injector cartridge is fluidly connected to the catheter 20 such that injectate is pumped from the injectate reservoirs 44 by the roller pump 46 and into a lumen of the catheter 20.

The sensor 28 is part of an electronics suite 60 which is configured to receive inputs from at least one sensor 28 and use that data to control the injectate flow rate generated by the pump 46. Other inputs may include flow, blood oxygen saturation, and ECG signals. Alternatively, the pump system and parameters may be under direct manual control for flow rates and flow-time waveforms, flow volumes/drug dose, and total systemic drug dose delivered.

Figure 2:
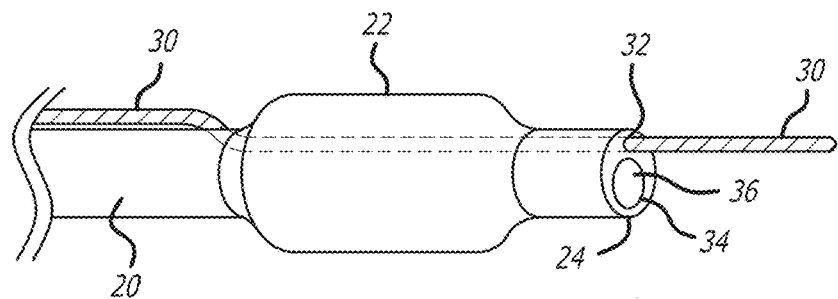
FIG. 2 is a perspective view of a distal end of an embodiment of a catheter of the invention.

FIG. 2 shows the distal end 24 of the catheter 20. The catheter may be configured to ride over a guidewire 30, such as a rapid exchange guidewire, via a guidewire lumen 32 formed in the sidewall 34 of the catheter and exiting just proximal to the balloon 22. A main lumen 36 extends the length of the catheter 20 and is in fluid communication with the injector cartridge 42. The main lumen 36 is thus configured to carry the injectate from the proximal end of the catheter to the distal end or through the many injectate infusion ports 26, if so configured. If the latter, the distal end 24 of the catheter is closed and the injectate ports 26 (FIG. 1), would consist of a series of small holes that serve to disperse pressure energy by creating a spray effect, with turbulence dispersing the energy. The injectate ports 26 may vary in size and angle to create a uniform cylindrical or circular infusate pressure spray against the vessel wall, and may also cause a centering effect that keeps the distal end 24 of the catheter centered within the native vessel.

Figure 3:
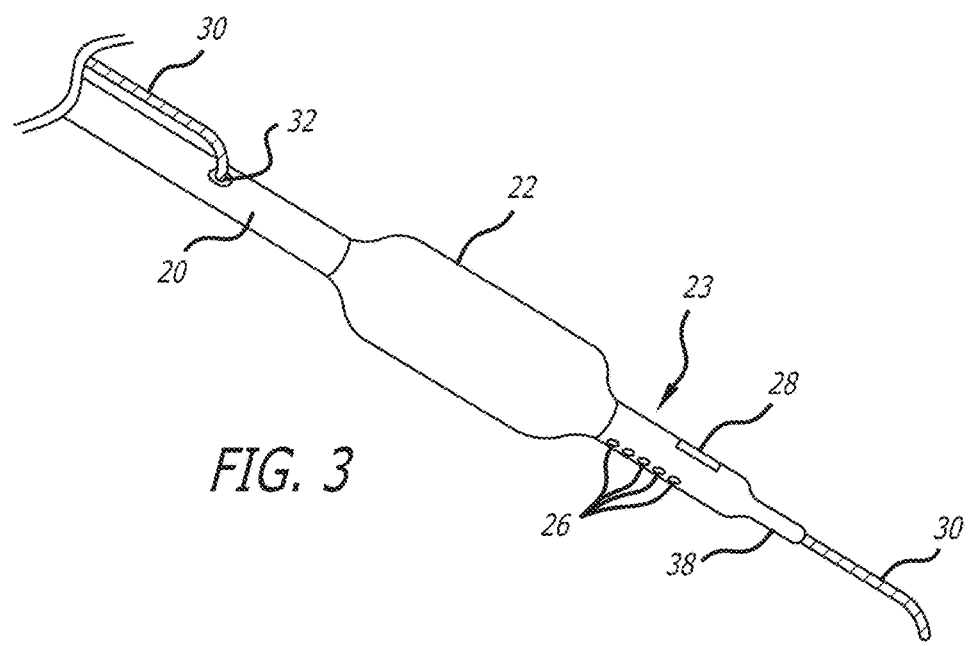
FIG. 3 is a perspective view of a distal end of an embodiment of a catheter of the invention.

One embodiment of a distal end 24 of the catheter is shown in FIG. 3. This embodiment shows a rapid exchange guidewire 30 which is routed through a guidewire lumen 32. The guidewire lumen 32 enters the catheter 20 proximal of the balloon 22 and exits distally through an elongated reduced diameter section or skive 38. In one embodiment, the skive is longer than about 1.5 cm and provides guidance for the occlusive balloon 22. The skive 38, due to its reduced diameter, also permits entry into branch vessels and stabilization therefore sensing vascular resistance in small vessels.

The configuration of the embodiment of FIG. 3 also shows flow holes 26 and a distal pressure sensor 28 on a distal balloon nose 23. This configuration ensures that the pressure sensor/transducer 28 is held in position away from the vascular wall. If the pressure transducer 28 were to be pressed against the wall, which neutralizes its ability to accurately measure pressure in the lumen of the blood vessel. The balloon holding the pressure transducer in mid-lumen is a distinct advantage to this configuration as it will not allow the transducer to damp against other objects such as occurs against the vessel wall itself.

Infusion ports for the therapeutic and diagnostic liquid are placed either near or far from pressure transducer 28. If the infusion ports and their exit distal to the balloon are too close to the pressure transducer, artifacts may be induced from fluid jet kinetic energy impinging on the transducer. For this reason, a finite distance between the transducer and the infusion ports is essential to optimize measurement of distal pressure.

Figure 4:
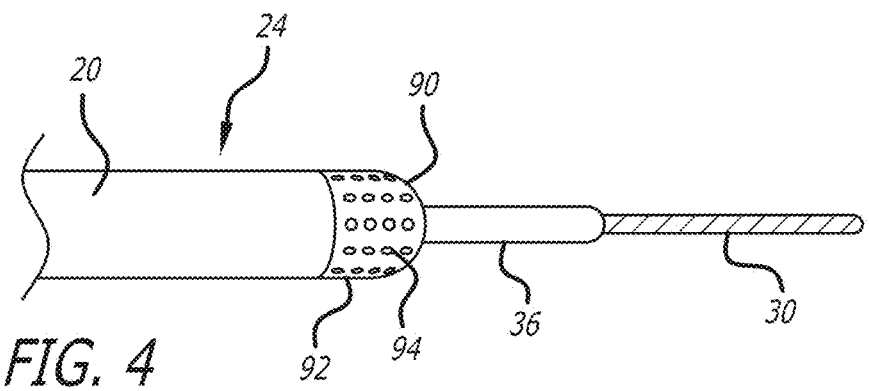
FIG. 4 is a perspective view of a distal end of an embodiment of a catheter of the invention.

FIG. 4 shows another embodiment of a distal end 24 of the catheter 20. The distal end 24 of the catheter 20 of this embodiment has a diffusion tip 90. The diffusion tip 90 may be conical or rounded and may taper down to a skive 36 as shown. Balloon inflation is conducted using a fluid preferably consisting of a standard x-ray contrast and any other fluid, typically in a 2:1 ratio. The purpose of diffusion holes is to reduce the flow energy in the infusion as it exits the infusion ports. Reducing the energy is accomplished by providing the diffusion tip 90 with a plurality of holes that are small enough to elevate Reynolds numbers and induce turbulence which disperses and diffuses flow and so dissipates energy safely. Diffuse flow through the tip 90 is "soft" and prevents the occurrence of damage that can be caused when high-energy jets impinge on the surrounding blood vessel walls. The above methods, to diffuse injectate flow create a cloud-like mass of infusate, optimal for safely and effectively rapidly introducing a therapeutic or diagnostic fluid.

The holes in the diffusion tip 90 may be sized and directed such that the infusate mass is directed distally downstream instead of radially. This configuration ensures that the infusate is delivered downstream to the target location and not inadvertently into the tissue surrounding the distal end 24 of the catheter 20. For example, the holes may be oriented to create a turbulent vortex that directs the infusate downstream and minimize outward forces on the vessel walls. In another embodiment, the holes are placed in a hybrid configuration, such that circumferential holes, which are relatively small, preventing forceful jetting yet have strong exit capabilities to create a passive, but not injurious, fluid barrier between the artery wall and the infusion ports thus creating centering. Distal, more axially directed holes 94 are provided with relatively larger diameters to create a second fluid configuration that is ideal for infusion into the vessel, and at the same time not injurious as it is being held away from the vessel wall by hydrodynamic forces from the smaller, circumferential holes 92.

Figure 5:
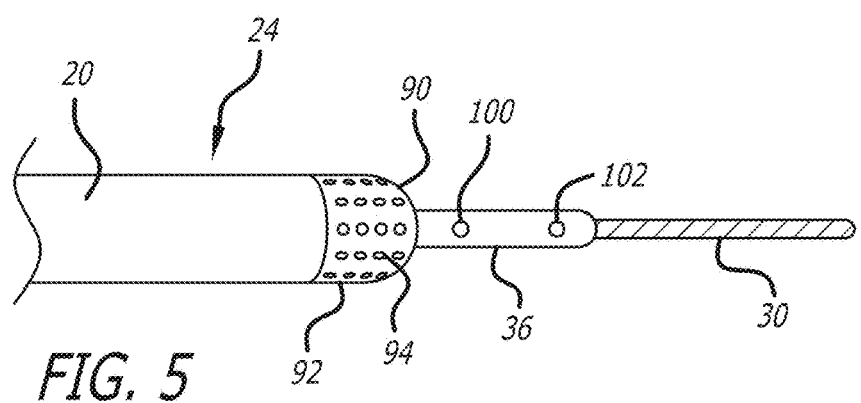
FIG. 5 is a perspective view of a distal end of an embodiment of a catheter of the invention.

FIG. 5 shows a distal end 24 of the embodiment that is similar to that of FIG. 4 with the addition of distal pressure/temperature sensors/transducers 100 and 102. Pressure/temperature transducers 100 and 102 are preferably mounted greater than 1 cm apart longitudinally. This embodiment and configuration permits measurement of axial intravascular (longitudinal) pressure gradients. Alternatively, the sensor can be able to measure pressure and temperature at the same time for instance by using an optical sensor. Utility of longitudinal pressure and temperature drops are key to understanding the relationship between vascular/arterial intake size and distal flow needs as measured by microvascular resistance.

This dual longitudinal distal sensor configuration is useful for measuring coronary artery physiology. For example, fractional flow reserve (FFR) is a parameter useful to determine the hemodynamic significance of a coronary artery stenosis. This measurement is the fractional longitudinal pressure drop across a coronary artery and plaque system at maximum distal vasodilation.

The two-linear pressure transducer configuration facilitates this measurement without the need for maximum vasodilation. Deterministic coronary flow injection by pump and pressure measurement from the flow allows simple and direct stenosis and hemodynamic quantitation. In this application of the invention as in FIG. 6, a stenosis S is approached proximally and the balloon 22 is seated proximal to the stenosis. The guidewire 30 and skive 38 with the pressure distal pressure transducer is advanced through the stenosis and stabilized in that location. The first distal pressure transducer 100 is on the proximal side of the stenosis/plaque while the second distal pressure transducer 102 is on the distal side of the stenosis. The occluding balloon 22 is inflated, and one or more physiologic flow rates are infused while measuring the pressure drop across the two transducers 100, 102. This pressure measured drop is directly proportional to hemodynamic stenosis resistance. Other important physiologic parameters are similarly measured, including coronary flow reserve (CFR), and true microvascular resistance as described within this application.

Dual pressure methods avoid the necessity of pharmacologic maximum vasodilation requiring intravenous or arterial vasodilatory agent. The invention achieves maximal vasodilation through balloon occlusion initiating temporary myocardial ischemia, the most powerful microvascular vasodilatory stimulus known. The invention eliminates pharmacological vasodilation otherwise required in coronary physiology assessment.

Another advantage of the invention and use method allows true hydrodynamic resistance quantitation, which can be converted to fractional flow reserve with mathematical transformation. The invention and method teach novelty for coronary artery pathophysiology assessment, and adds true hydrodynamic resistance, currently unmeasurable.

Figure 7:
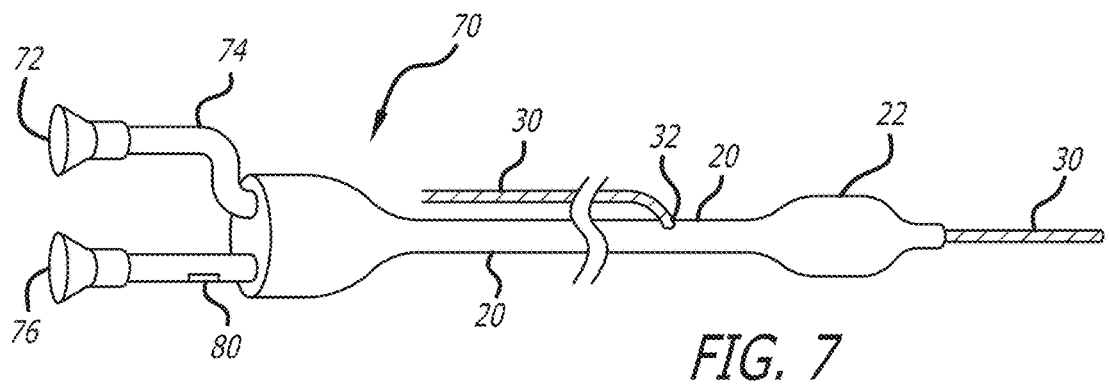
FIG. 7 is a perspective view of an embodiment of a catheter of the invention.

FIG. 7 is a detailed view of an embodiment of the proximal end 70 of the catheter 20. In this embodiment, the proximal end 70 includes a balloon connection 72, which connects a pressurized fluid source to a balloon lumen 74. The balloon lumen 74 extends to the balloon 22 for inflation thereof. Preferably, the balloon lumen 74 is sized to permit rapid inflation of the balloon, preferably achieving full inflation within three seconds and rapid deflation, within six seconds. The occlusion balloon may be manually inflated and deflated using an indeflator or using an automatic balloon inflation/deflation system. Also included is a drug connector 76, which connects the main lumen 36 to the pump 46.

The embodiment of FIG. 7 includes a proximal pressure sensor 80, in addition to, or instead of, the distal pressure sensor 28 shown in FIG. 1, for example. The pressure measured by proximal sensor 80 is pressure inside the lumen 36, and is a function of the force created by the pump 46 and the resistance offered by the catheter lumen 36 as well as the resistance to flow created by the environment outside the distal end 24 of the catheter 20.

Figure 8:
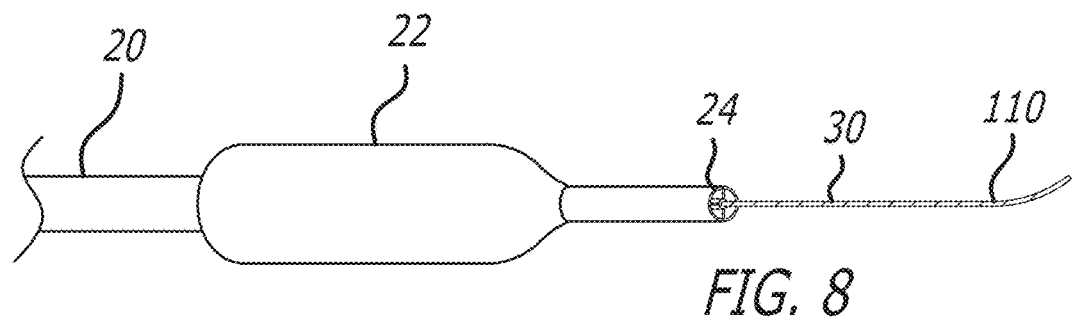
FIG. 8 is a perspective view of a distal end of an embodiment of a catheter of the invention.
Figure 9:
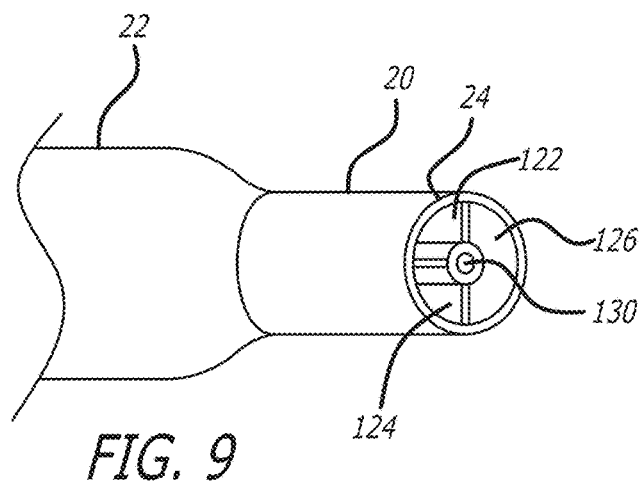
FIG. 9 is a perspective view of a distal end of an embodiment of a catheter of the invention.

FIGS. 8 and 9 show an embodiment of a catheter 20 that includes a suction feature. The catheter 20 includes a balloon 22, a distal end 24 of the catheter 20 that extends beyond the balloon 22, and a guidewire 30 extending therefrom. This embodiment includes a distal pressure sensor 110 that is located on the guidewire, rather than on the catheter 20, as in previous embodiments. This modification may be incorporated into any or all embodiments described in this application. The pressure sensing guidewire is useful in this configuration to monitor distal flow for possible emboli or other hemodynamic complications.

As best seen in FIG. 9, a configuration of a catheter 120 is shown that includes multiple lumens, including an infusion lumen 122, a balloon inflation lumen 124 (which would either be closed at the distal end 24 or not extend all the way to the distal end 24), a suction lumen 126, and a guidewire lumen 130.

Negative pressure on the catheter via pump has several benefits. As microvascular clot and obstruction is lysed, undesirable biologic and chemical byproducts such as lytic clot material and embolic debris may be produced. Clot lysis removal will be achieved by applying catheter suction.

One way to accomplish debris removal is to reverse the pump flow thereby creating a negative pressure, with retrograde fluid and blood flow from the artery back into and through the catheter. Using a suction catheter provides faster pulsatile cycling, also antegrade irrigation. In this manner, clot and lytic thrombus extraction is possible on a continuous basis with clot lysis followed by clot and lysed byproduct suction.

The lytic/suction configuration for eliminating and removing debris products can be accomplished as part of the invention. Incorporating one-way valves (check valves) in the catheter connector from the pump feeding the catheter. A one-way valve inserted into the suction lumen prevents infusion flow entering. With applied negative pressure flow is directed to the exhaust port, entering the catheter through the infusion ports. In this context blood may be infused antegrade and thrombus products removed after lysis.

Figure 10:
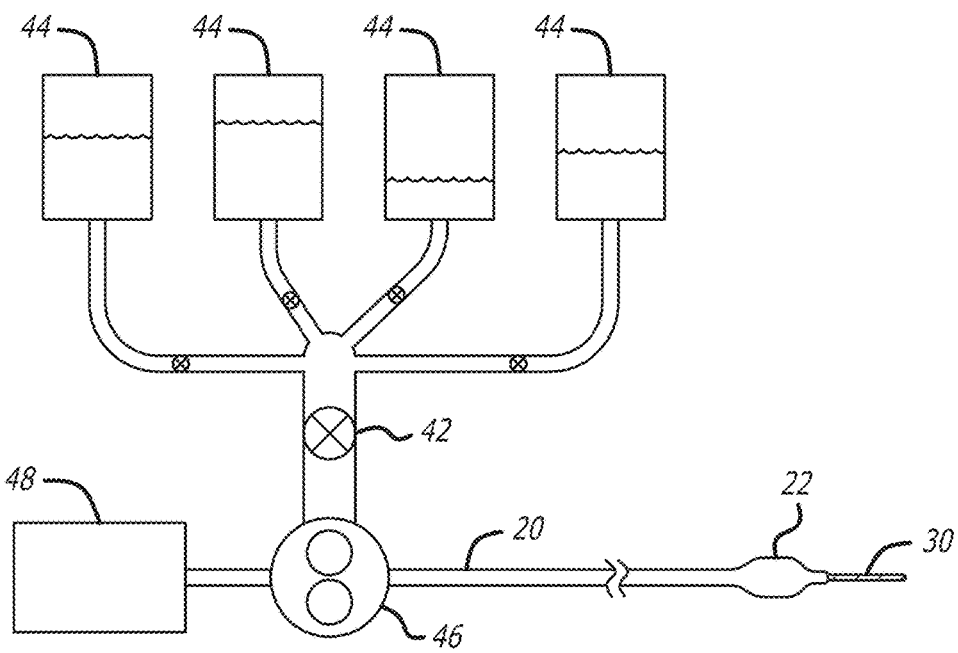
FIG. 10 is a diagram of an embodiment of a system of the invention.

FIG. 10 is an embodiment of the complete system 10 of the invention for treating occluded myocardial or other organ (lung, brain, kidney, liver, any skeletal muscle) microvessels that includes a plurality of injectate reservoirs 44 and a selector switch 42 that allows one or more of the injectate fluids contained in the reservoirs 44 to be administered through the catheter, driven by the pump 46. The injectate fluids may be diagnostic or therapeutic.

The catheter 20 may include one or more lumens to permit pressure sensing with controls and signals, single or multiple drug or fluid infusion ports, and guidewire. This can be in either an over-the-wire or rapid exchange configuration at the distal end. The pump 46 and optionally the switch 42, may be controlled by a controller 48 that may be electronic or manual.

The controller 48 may operate in either an open loop or a closed loop configuration. Infusion parameters used by the pump may be fixed and/or manually controlled without physiologic feedback in an "open loop" configuration. Alternatively, infusion flow and pressure parameters may be feedback controlled (servo- or synchro-feedback system) in a "closed loop" configuration. In this embodiment, the physiologic parameters such as pressures (infusion flow, physiology of the heart chambers) are used as inputs by the controller 48 to change the commands given to the pump 46 and/or the switch 42. These physiologic parameters may also be acquired, for example, from other chambers or structures including, but not limited to, the Left Ventricle, Left Atrium, Pulmonary Arteries or Veins, Right Ventricle, Right Atrium, Central veins, volumes of such chambers, mechanical or physiologic function of such chambers, or bioelectric signals (EKG, myocellular function, Electromyography (EMG), neurologic/neuronal including signals derived from the autonomic nervous system).

Figure 24:
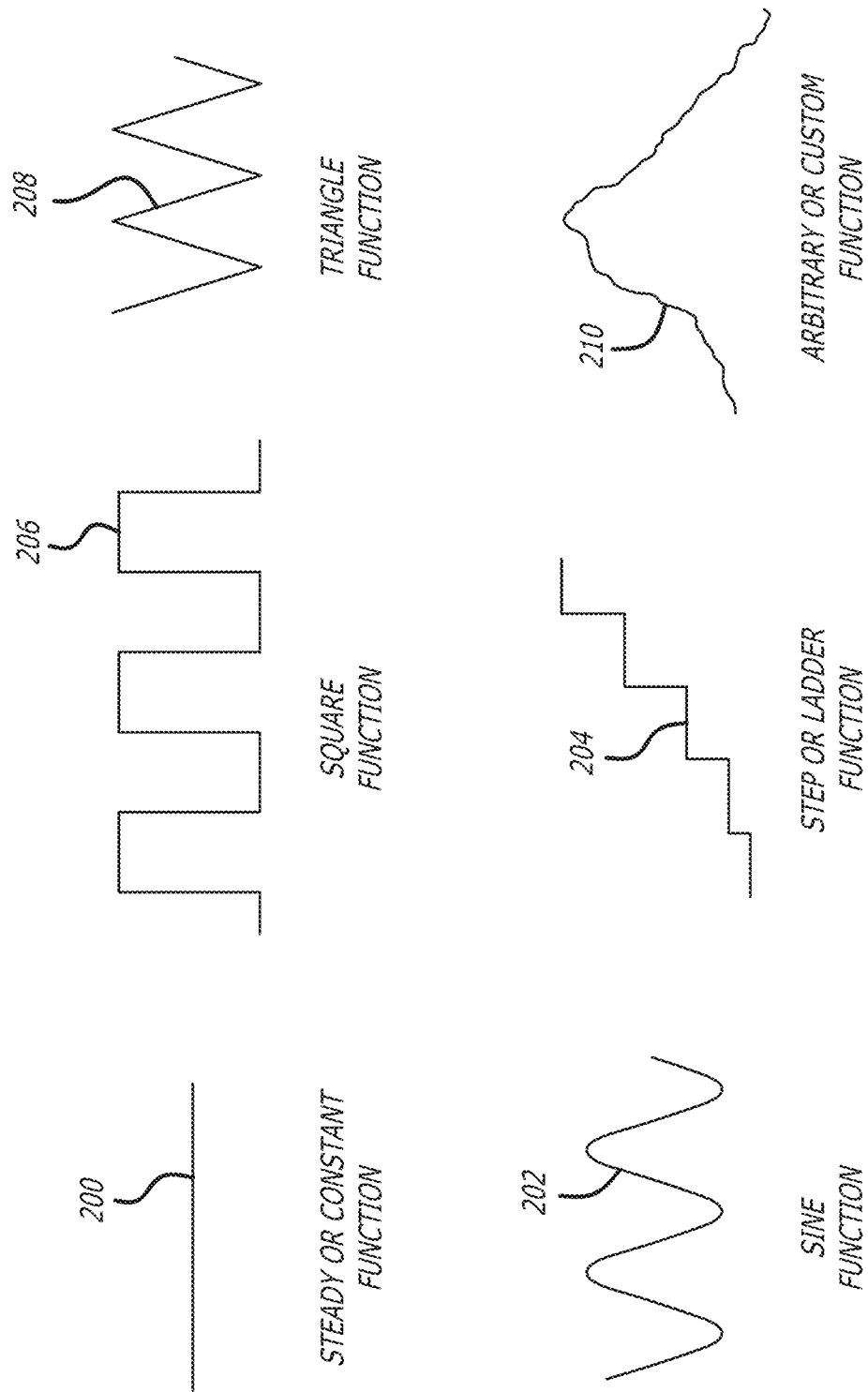
FIG. 24 is a graphic showing various waveforms.

In one embodiment, the controller 48 is programmable such that various waveforms (seen in FIG. 24) may be inputted and represent resulting flow patterns to be executed by the pump 46. The infusion waveforms may include, but are not limited to, constant 200, sinusoidal 202, step-function 204, square wave 206, sawtooth or triangle function 208, or an arbitrary or custom function 210. The constant or steady waveform 200 is a waveform in which the flow is held constant. The flow may be zero or any other desired rate from the pump 46. The square wave 206 is that in which the flow alternates between 2 discrete values, which may be zero, negative, or positive, and at any practical period/frequency. The triangle wave 208 is a waveform in which flow is linear up to a peak, and linearly decreasing. Baseline may be zero, positive, or negative. The sine wave 202 is a wave in which flow is sinusoidal with any phase. Baseline may be zero, positive, or negative. The step or ladder function 204 is a waveform in which the flow increases in discrete steps, monotonically increasing, decreasing, or a combination of these. Flow may go to zero after the peak, or any other rate. The arbitrary waveform 210 comprises any arbitrary flow rate in time, may be period or non-periodic. Additionally, as described in reference to FIG. 9, the pressure created by the pump may be positive (infusion) or negative (suction). Alternatively, the controller may be programmed to vary flow to maintain a constant pressure that may equal zero, or a positive or negative value that holds the flow in the vessels at zero.

Figure 11:
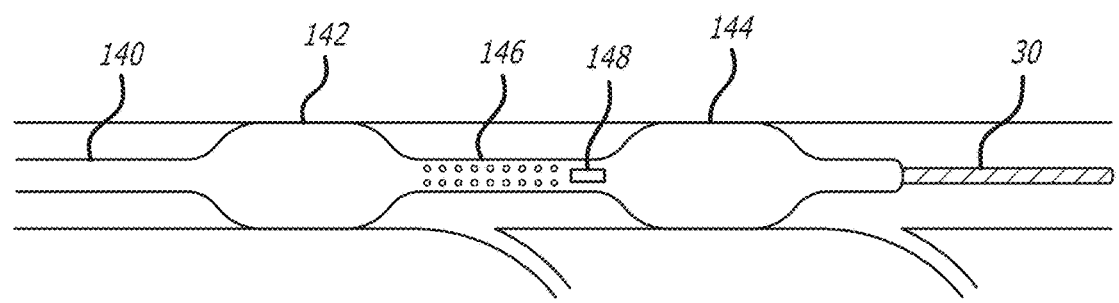
FIG. 11 is a side view of a distal end of an embodiment of a catheter of the invention being used in a vessel.

FIG. 11 is an embodiment of a catheter 140 facilitating microvascular resistance measurement and therapy over a short segment. The catheter 140 includes a first balloon 142 and a second balloon 144 spaced apart from the first balloon 142. A plurality of infusion holes 146 reside between the two balloons 142, 144.

Rather than assessing all microvasculature distal to an occlusion balloon, this embodiment of the invention allows assessment and therapy of microvessels and myocardium supplied by the limited arterial segment between two or more balloons. Controlled fluid infusion into the interballoon segments is thus highly limited and yields precise physiologic information based on anatomy. For example, this configuration could assess and treat myocardium subtended by a single branch vessel such as a diagonal artery. It thus allows only microvessels depending on that epicardial arterial segment, because the remainder of the microvessels are not infused as they are blocked from flow by balloon inflation. This is an extension of the one balloon system of the infusion and pressure sensing catheter invention.

The longitudinal interval between balloon pairs contains fluid infusion holes 146 and one or more pressure transducers 148. In one embodiment, the balloon inflation lumens are connected to a single inflation source so they inflate simultaneously. At inflation, the dual balloon configuration creates an isolated blood vessel segment, which can be located at any point in the vessel. Known flow infusion rate at resulting pressure yield very accurate measurement of microvascular resistance and function (Resistance, autoregulation, endothelial function). This configuration of the invention makes possible sequential assessment of MVO and other characteristics (autoregulation health, myocardial contractility, ischemic potential).

Therapeutic agents for clearing MVO may be any combination of the following. These agents are for anti-thrombotic, thrombolytic (anti-fibrin), platelet lytic, anti-inflammatory agents, and cooling. Any of the above agents may be mixed with X-ray contrast as a carrier to provide visualization. This mixing may be performed with in an in-line mixing chamber, or be mixed at the console level. The mixing may be console and computer controlled, a process that allows differing dosing combinations as desired.

Non-limiting examples of agents to be used as injectates/infusates are as follows:

Anti-Thrombus (Platelet, fibrin, leukocyte bound thrombi).
 1. Hirudin/Hirulog/BiValrudin, Anti-Xa, Reopro/Abciximab
 2. Other Anti-thombotic Agents: Anti-factor X, factor VII, other anti-GpIIB/IIIA agents, Tick Anticoagulant Peptide, echistatin, Integrilin, PPACK, DPG peptide inhibitor, TNK, streptokinase, urokinase, rTPA, adenosine, nitroglycerin, sodium nitroprusside, nicorandil, Hirulog, Bivalrudin, ReoPro, eptifibatide, TAP (tick anticoagulant peptide), Unfractionated Heparin, LMW Heparin, Argatroban, Hirudin, Refludan/Lepirudin (Berlex), Desirudin, ABCIXIMAB, Eptifibatide, Tirofiban, Alteplase, Reteplase, Tenecteplase, Factor Xz, rivaroxaban, Fodaparinux, adenosine, anti-PMN antibodies, anti-leukocyte antibodies, quinolone agents, nitrogen mustard, hydroxyurea, anti-serotonin agents, such as cinanserin, pizotifen, cyproheptadine, lysenyl, mianserin, methysergide, promethazine, octreotide, trypsin, papain, chymotrypsin, lidocaine, quinidine, amiodarone, procainamide, propofenone, and beta blockade.
 3. Anti-integrins including but not limited to CD11b/CD18, CD11c, GPRP-peptide, GpIIb/IIIa antagonists, direct thrombin inhibitors, Abciximab, rTPA, TNK, streptokinase, urokinase, Unfractionated heparin, LMW heparin, tirofiban, lamifiban, orofiban, xemlofiban, and Factor Xa inhibitors
 4. Anti-Edema agents including Hypertonic saline or any other hyperosmolar agents such as Mannitol, Lidocaine, Adenosine, Cooled fluid (25-37 degrees C.), hyperoxygenated fluids.

The therapeutic agents may be combined for synergistic enhanced efficacy. Methods to mix agents and vary the mixture ratio and create novel dosing include:
 1. Each Drug/agent from a separate infusion pump filling a mixing chamber at differing rates depending on the desired ratio.
 2. Mixture is calculated by flow rates/ratio of carrier:drug
 3. Drug/therapeutic to the carrier stream in desired/changing combinations
 4. Infusion (diagnostic or therapeutic) is independently set
 5. A carrier is used, and has important biocompatibility. Such a carrier could be Ringer's Lactate, Balanced crystalloid of any commonly used agent.

Other therapeutic options are facilitated by the invention, including but not limited to: Myocardial prevention, Myocardial Salvage, and Reperfusion Injury Mitigation. Generally, the purpose of rapid blood flow restoration to infracting and ischemic myocardial tissue is to 1) prevent additional ongoing injury, 2) salvage muscle that has already been injured but not irreversibly killed, and 3) mitigate reperfusion injury. Reperfusion (reoxygenation) injury causes tissue damage as blood supply returns after ischemia.

The invention is an ideal method to treat muscle or tissue following ischemic or anoxic insult, and provides strategy to infuse agents for myocardial preservation and salvage. Cardioplegic strategies represent additional therapeutic options, with a purpose of lowering myocardial energy expenditure in focal regions of the heart. This method will partially "paralyze" myocardial contraction in a segment of myocardium. This will 'rest' a focal area of the myocardial infarction, lower oxygen need/consumption and avoid muscle cell death or severe ischemia. This may be achieved in several ways:
1. Electrolyte Solution
2. Electrical blocking agents
3. Electrical-mechanical decoupling
4. Cooling the muscle to low temperature with pharmacologic agents.

Figure 12:
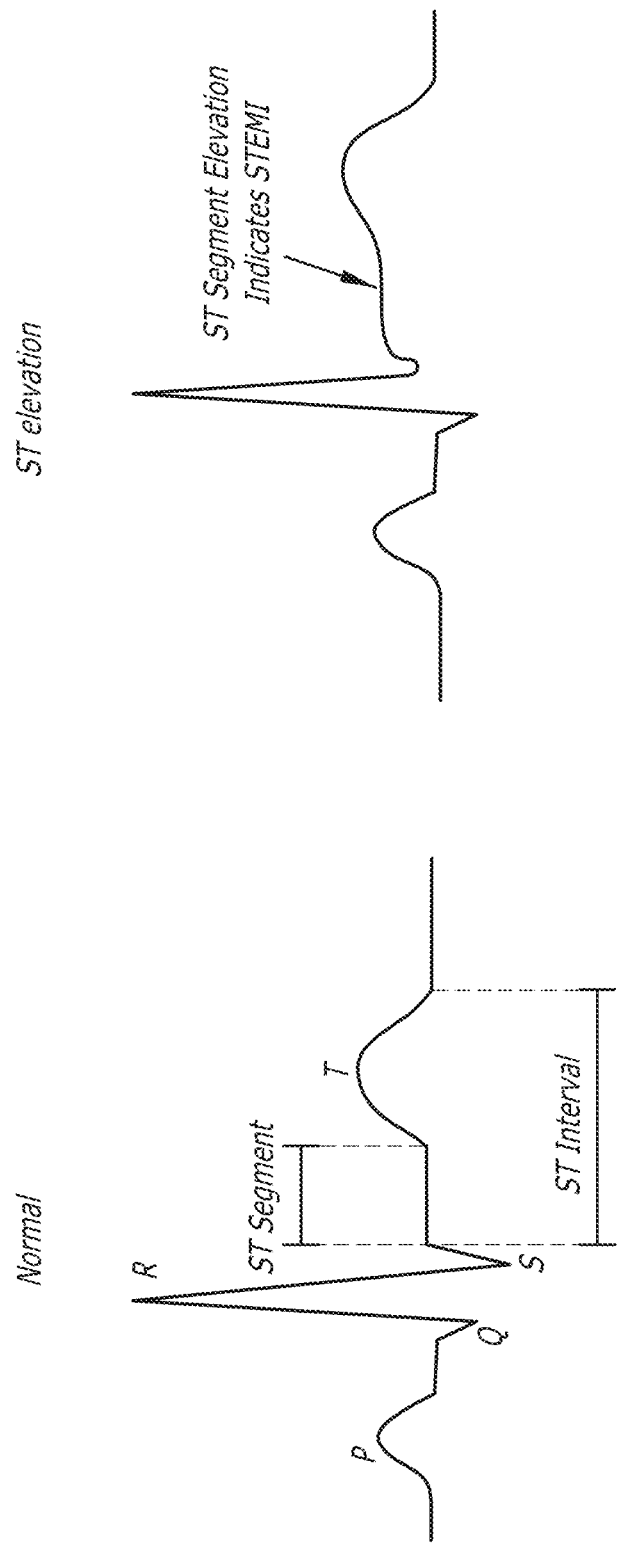
FIG. 12 is a comparison between a normal and an ECG with ST elevation.

Having described the general components of the various physical embodiments of the invention, the methods and uses of the devices may now be described. Turning to FIG. 12, there is shown a diagram of a two simplified ECGs showing the various components and comparing a Normal ECG to an ECG of a STEMI/Heart Attack patient having elevated ST to highlight the ST segment. Electrocardiographic signs of acute transmural myocardial infarction (heart attack) are ECG tracings with ST segment elevation (STEMI). The ST segment is the repolarization portion of an ECG as shown in FIG. 12. ST Segment elevation is defined from the ECG when the ST segments or one or more surface leads show abnormal ST elevation above baseline.

Figure 13B:
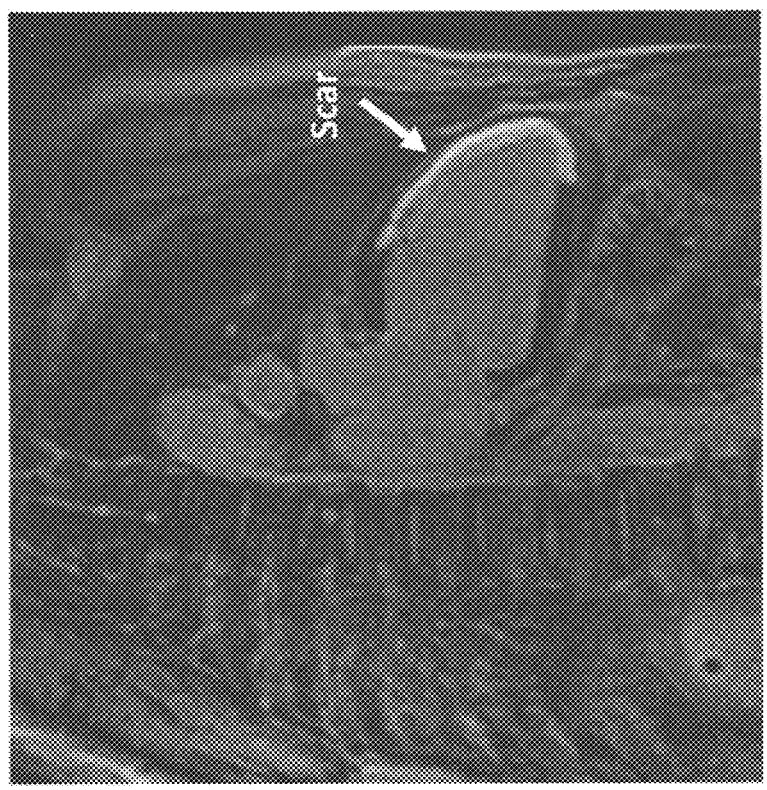
FIG. 13b is a frame of the cardiac gadolinium contrast MRI scan of the patient of FIG. 13a taken 6 months later.
Figure 13A:
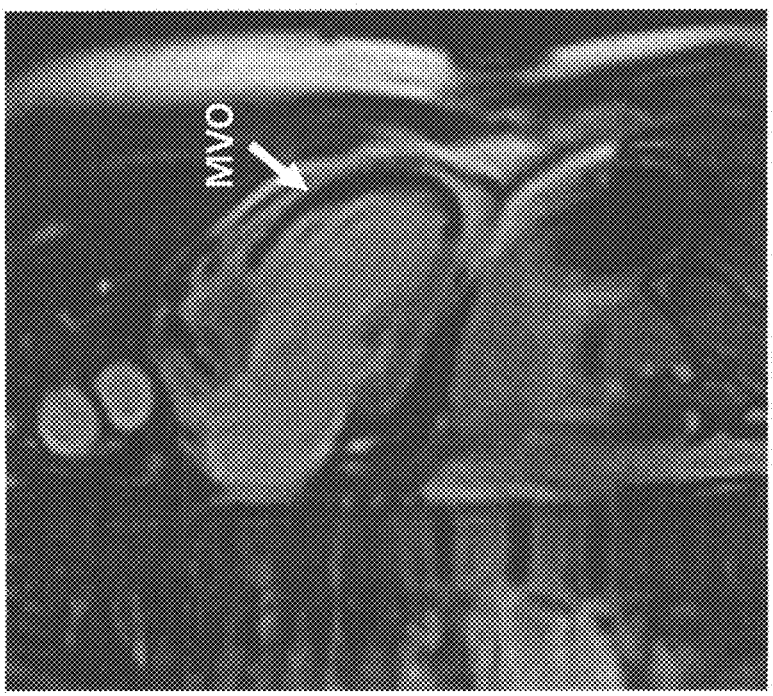
FIG. 13a is a frame of a cardiac gadolinium contrast MRI scan of a patient taken 3 days after a heart attack.

FIG. 13a is a frame from a cardiac gadolinium contrast MRI scan of a patient 3 days after STEMI. It shows MVO as very dark regions of heart muscle resulting from no blood or contrast flow into the microvasculature.

Figure 6:
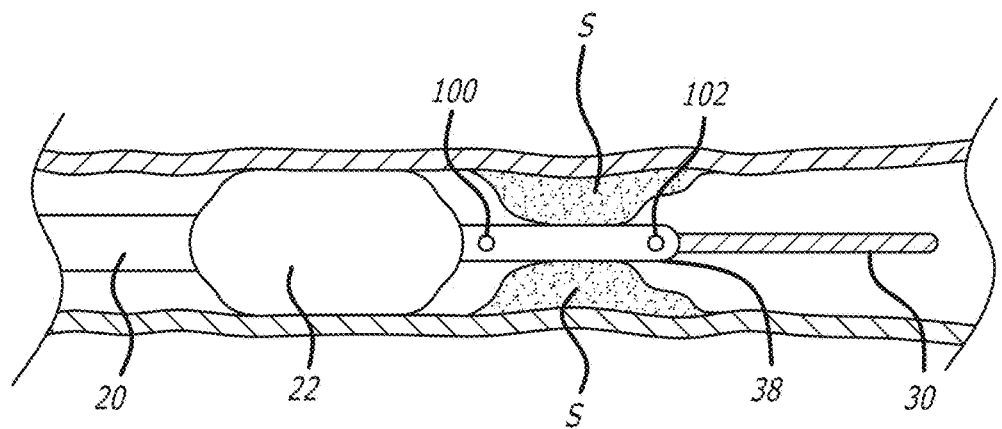
FIG. 6 is a perspective view of a distal end of an embodiment of a catheter of the invention being used in a blocked vessel.

FIG. 13b is a repeat scan of the same patient heart of FIG. 13a 6 months later showing dense heart scarring from dead muscle caused by the MVO. The dead muscle becomes scar, visible in the MRI scan as a white line.

Figure 14:
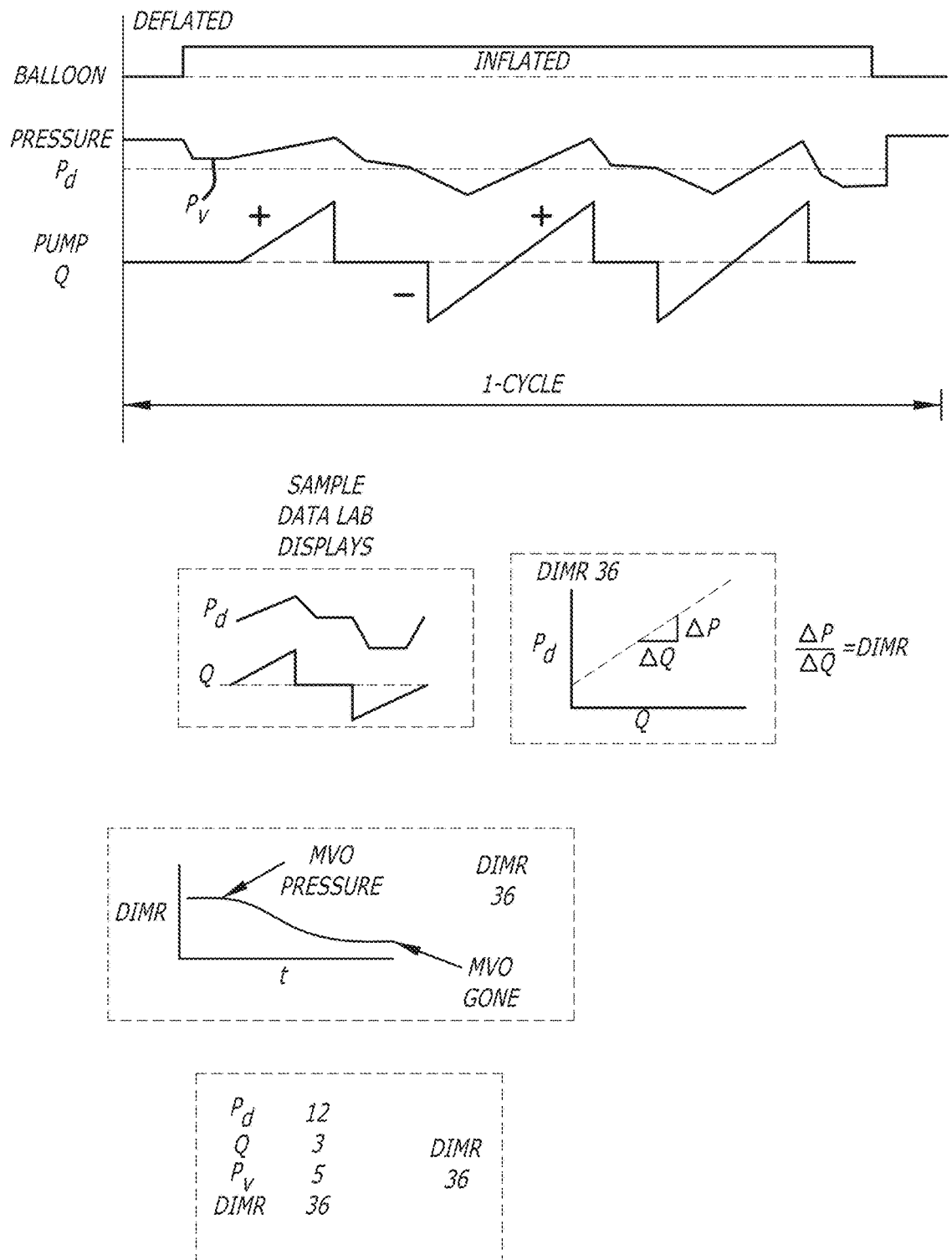
FIG. 14 is a diagram of various parameters of a cardiac cycle during execution of an embodiment of a method of the invention.

Turning to FIG. 14, there is shown a diagram of a proprietary cycle of therapy or diagnosis. A cycle is defined as events occurring during the time of a complete occlusive balloon inflation. During this time waterfall pressure is measured. Waterfall pressure is the pressure distal to a complete balloon obstruction in a coronary artery. As seen in this diagram flows may be positive, negative, or both combined in series through time. Another important context as mentioned above. Therapy is initiated, with infusion delivering high local drug concentration to occluded microvessel ostia, and held in place by pump flow cessation. The resulting dwell time permits native pump action to drive therapeutic agent into the occluded microvessels.

During the dwell time, positive pressure remains and results from the Waterfall Pressure. Therapeutic agents are thus pumped into the occluded vessel, a process augmented by the waterfall pressure. Waterfall pressure is cyclical due to heart contraction, which performs auto-agitation of the local environment. This also functions to insinuate therapeutic agent into the occluded vessel. This pressure is not so high as to drive flow through into and through patent vessels. Flow cessation and resulting waterfall pressure causes intramural vessel capillaries and collaterals collapse due to the Starling Resistor effect. Microvessel collapse causes very high capillary resistance, a phenomenon tested already in an animal model while preparing background material for this application.

Pump created flow cessation within an injection cycle is central to the invention. It equalizes resistances between patent and occluded microvessels. Microvessels have been shown to have antegrade flow that is very slow, but will carry drug into the occluded regions and facilitate lysis.

FIG. 14 demonstrates the pump used as an agitator, and alternatively for cyclic variation in intra-myocardial pressure. Agitation is also a method that pumps therapeutic drug flow to obstructed microvessels.

This figure also illustrates methods of the invention for Direct and "true" microvascular resistance measurement. It shows direct flow infusion, a microvascular bed receiving that flow infusion which then develops a pressure proportional to the hydraulic resistance of the microvascular bed. This is a very accurate way of measuring directly hydraulic resistance or impedance in the microvasculature, a method no prior technology has been able to accomplish.

Calculations are as follows, whereby the instantaneous derivative of pressure change by infused volume change measures direct IMR (DIMR).

$dP/dQ'$-DIMR
Pd'-12
Q'-3
Pv'-5
DIMR-36

Figure 15:
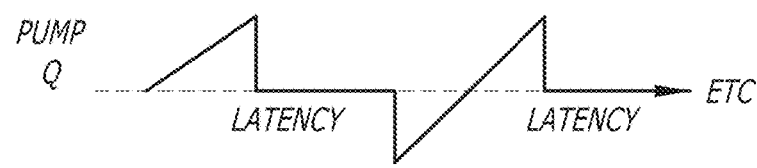
FIG. 15 is a graph of pump flow rate over time according to an embodiment of a method of the invention.

FIG. 15 is a graph that demonstrates a latency as part of the invention where the pump ceases and holds infusate within the vessels, not adding additional therapeutic agent to the system. The purpose is to hold flow to zero and allow the agent to be driven into occluded or partially occluded microvessels via the pumping action of the myocardium (alternately raises and lowers interstitial pressure) and the waterfall pressure which drives therapeutic agent into the microvasculature.

The only limitation to occlusive balloon inflation is ischemia time as the distal myocardium becomes ischemic while the balloon is inflated. An alternative to prevent this ischemia is to infuse whole blood, disclosed in this application. Whole blood provides oxygenation as well as glucose and other important nutrients to muscle distal to the inflation balloon.

An aspect of this invention is to directly monitor myocardial ischemia via the distal guidewire, using it as an intracardiac ECG sensor. It is connected in a bipolar configuration to record an electrocardiogram from within a coronary artery. This is a sensitive method to determine local ST segment elevation and thus ongoing cell death. It also can measure ST segment depression representing myocardial ischemia. The intracardiac ECG is immediate feedback mechanism during the procedure. The intracoronary pressure wire may be used to deliver stents, for pressure measurement, and also for ECG and focal myocardial ischemia/infarction monitoring. In another configuration the wire may be covered using an insulating material, leaving only a tip or a small series of bare metal regions electrodes exposed on the guidewire. This becomes an electrocardiographic array on the guidewire which also serves as a pressure monitor and a guide for stent delivery.

Figure 16:
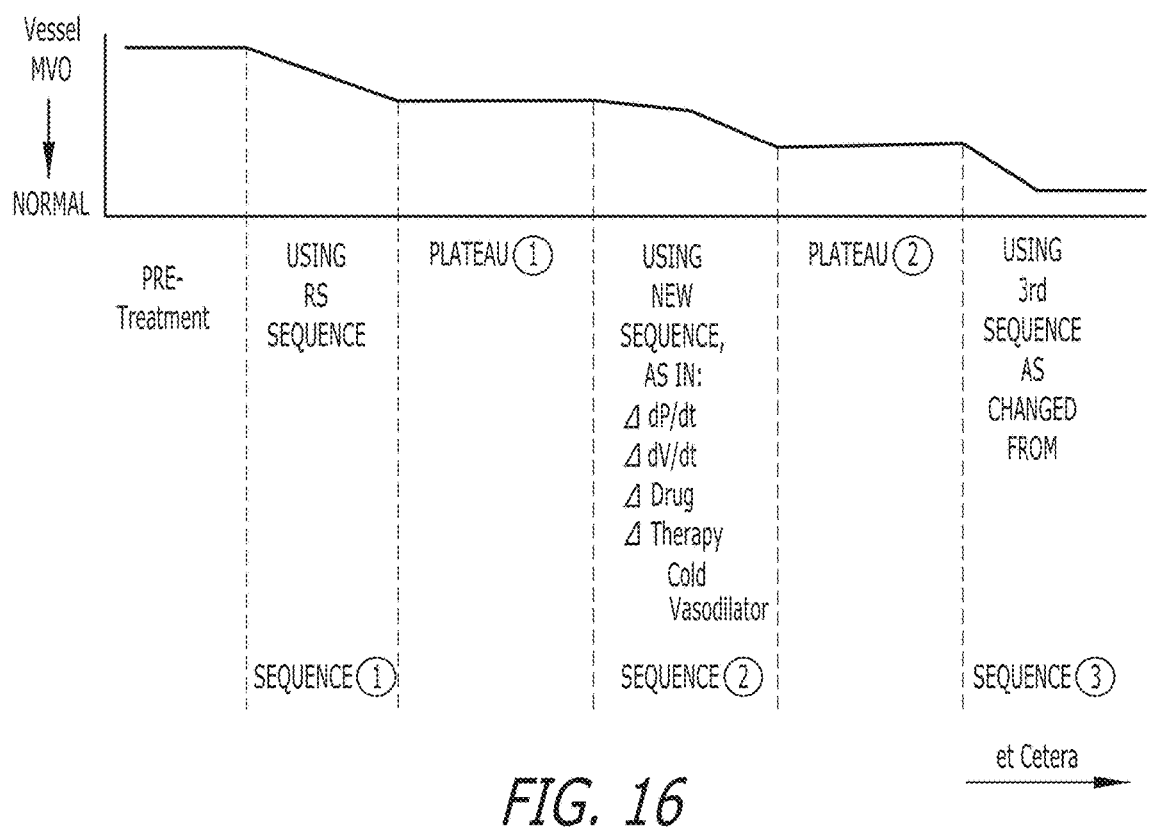
FIG. 16 is a graph showing the accumulative efficacy of repeated cycles of a method of the invention.

FIG. 16 shows how repeating the cycles as part of this invention progressively lyse and dissolve clot within microvessels until they are completely opened from the therapeutic infusion. In this method tau is a measure of obstruction, and intermittent tau measurement by occlusion balloon inflation yields updated information regarding opening the microvessels.

This invention also describes cyclic fluid delivery for therapy and measurement. Such a cycle entail therapeutic infusion, diagnostic infusion, flow cessation, and repeating the sequence at discretion of a human operator or via a preprogrammed automation. The decision process utilizes pressure, flow, and electrocardiographic evidence of improvement to determine microvascular obstruction status and to make decisions on repeating therapy and diagnostic cycles. In this way the decision to treat is based on efficacy at lysing the microvascular thrombus, where efficacy which is directly measured by the diagnostic component of this integrated therapeutic-diagnostic technology.

The electronic console may be triggered to begin a cycle, or alternatively may be separately programmed for parameters of acquisition flow-pump control and calculation of microvascular resistances and impedances.

This integrated system provides for high local drug concentration at the microvessel occlusion site, providing a method to enter drug into the slow flowing MVO vessels, and minimizing the systemic drug doses. Drugs and therapeutic agents in this strategy are powerful lytic and anti-thrombotic agents. Agents given in the therapeutic local process enter the MVO affected vessels slowly, as shown by MRI scans. These agents eventually enter the systemic circulation as they pass through the heart microvasculature, coronary veins, and into the systemic veins.

These agents are quite potent and have well defined maximal systemic dose that should not be exceeded or else risk dangerous systemic bleeding (into the brain, GI tract and elsewhere). The invention, by treating organ ischemia and infarction using dose feedback from flow/resistance real time measurement is a strategy for using the minimal effective dose through real time feedback. It thus minimizes systemic dosing and provides a safety factor for potential systemic lytic or therapeutic agent toxicity.

The invention provides for optimal dosing and more efficient delivery to the slow or semi-occluded microvasculature. Flow is slower (but present) in the occluded vessels compared with in the patent vessels and the strategy of this invention partially matches flow rates and permits targeted specific therapy into occluded microvascular blood vessels.

The strategy of the invention maximizes driving pressure—time integral for drug entering the microvessels, and equalizes dwell time at the ostia of occluded or slow-flow vessels.

Flow cessation as part of infusion maximizes dwell time, optimizes local dose and minimizing systemic dose, and intentionally prolongs flow entry into the microvasculature. This results from devices and hardware, software/programming, physical strategy and real time feedback using integral diagnostic methods.

Figure 17:
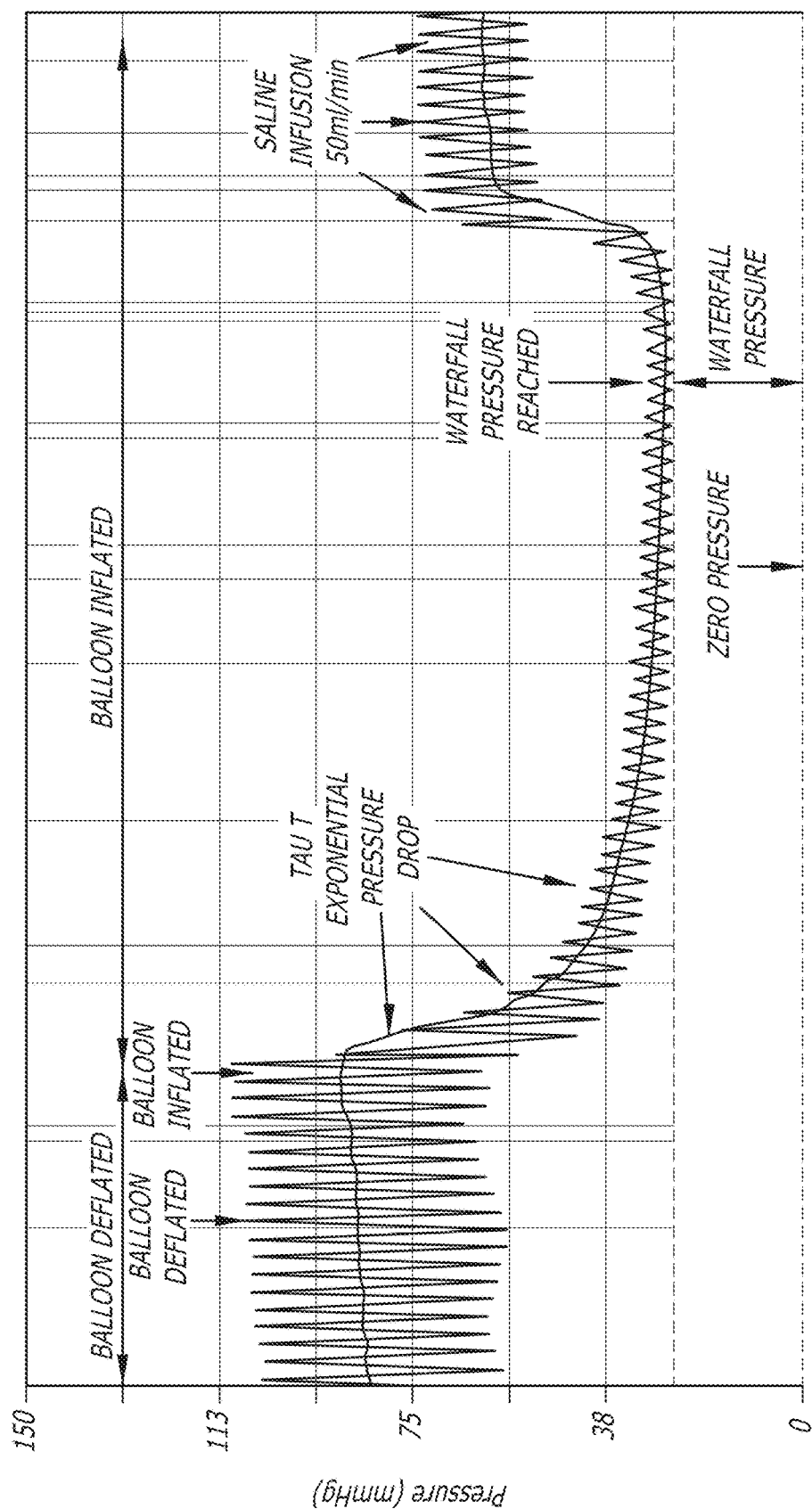
FIG. 17 is a pulsatile waveform representative of the type that would be analyzed using an embodiment of a method of the invention.

FIG. 17 is a pulsatile waveform recorded from a beating heart using an aspect of one method of the invention. The invention permits measurement of key heart functional parameters including integrity of both large and small blood vessels. The pressure transducer at the distal balloon records a pressure in the proximal coronary artery reflecting pressure in the aorta, the driving pressure for heart blood flow. As the occluding balloon inflates, it blocks this aortic pressure from impacting the pressure sensor. The pressure sensor thus measures intracardiac pressure waveforms. As the pressure waveform transitions from aortic driving to intracardiac, it follows a course that is monoexponential decay over time. The exponential time decay follows a method of the invention, tau. The exponential coefficient has units 1/sec. As the pressure decays It settles to an asymptotic value of lower pressure—the Waterfall pressure. The asymptotic waterfall pressure measures important heart functional parameters, including collateral blood supply to this region, and local myocardial pump contractility.

FIG. 17 also shows the pressure resulting from controlled flow infusion through the catheter infusion ports. Many substances may be infused per the invention, including Lacated Ringer's, solution, balanced saline (electrolytes, glucose), whole blood or blood products (Plasma, serum, red blood cells, platelets), Freon or derivatives, or any other biocompatible fluid. The fluid may contain any combination of drugs, and may also be temperature controlled to effect myocardial salvage.

Pump flow is defined at known and selectable values and carefully controlled by digital methods. This pressure resulting from controlled flow infusion is measured, and microvascular resistance directly calculated as Pressure/Flow. Increasing infusion flow permits measurement of microvascular resistance at multiple rates. This flow during balloon occlusion is an embodiment of a method to sense resistances, tau, and Waterfall pressure.

Figure 18:
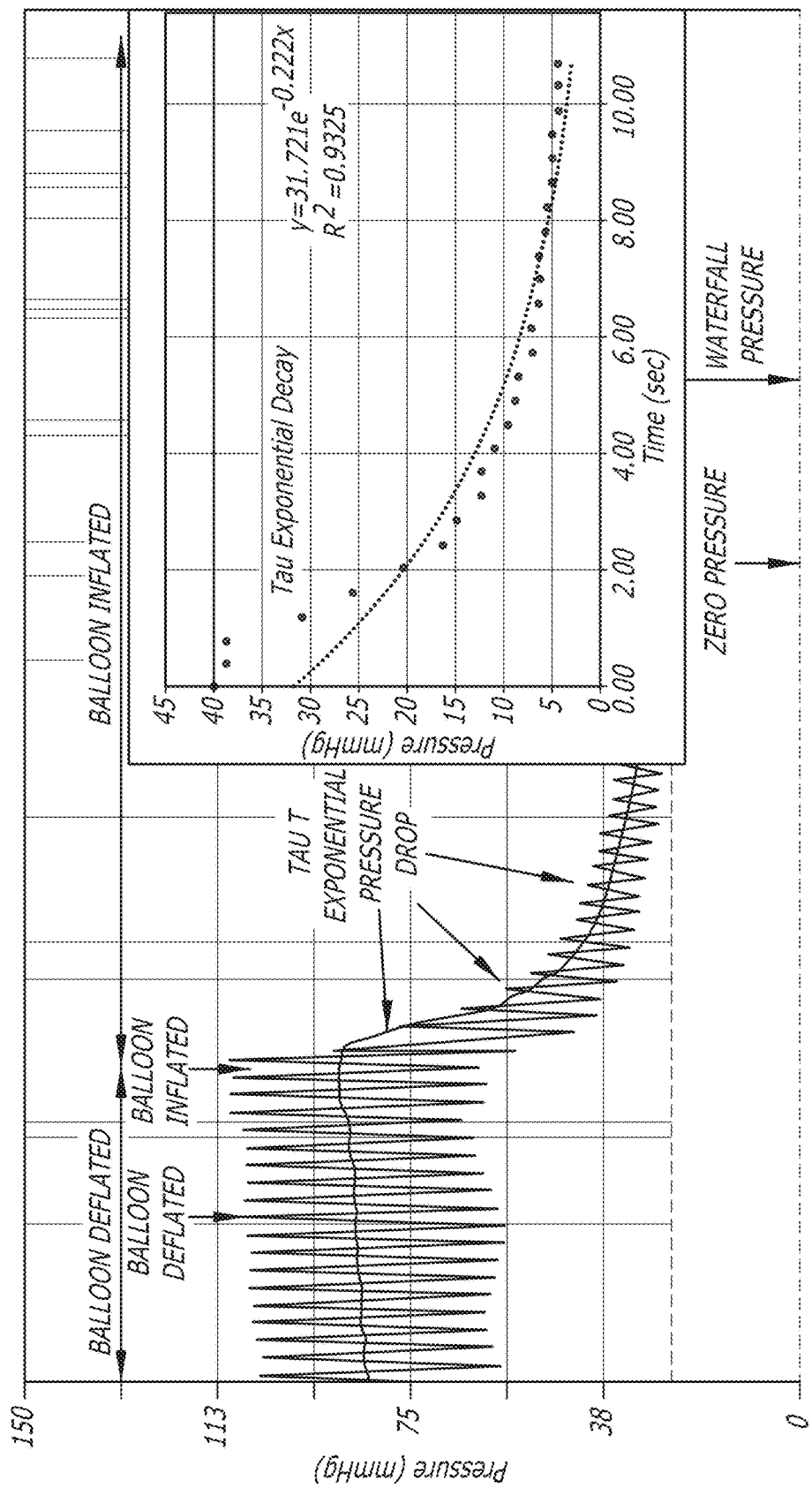
FIG. 18 is the pulsatile waveform of FIG. 3 with a graph insert showing the exponential decay of Tau.

FIG. 18 is the pulsatile waveform of FIG. 17 with an additional graph inset into the graph of FIG. 17. This chart was formed using a normal heart where the balloon of the invention was inflated with distal pressure measurement. Attention is focused on the pressure exponential decay immediately following occlusion balloon inflation. The inset graph shows the exponential fit to the pressure decay as it asymptotically approaches the waterfall pressure. Tau in this heart is $1/0.222=4.50$ seconds. Tau is a key variable of this invention, as it reflects blood draining from the heart and its microvasculature. Tau is critically dependent on microvascular integrity. Prolonged blood draining results in longer/larger tau.

FIG. 18 shows that prior to balloon inflation, proximal coronary artery pressure is measured. When the balloon inflates, it completely obstructs the proximal pressure, and causes distal coronary artery pressure to drop. The pressure distal to the balloon begins to drop and follows a decreasing function with a simple monoexponential time course. The time constant is characterized by the variable Tau. The pressure reaches the asymptotic Waterfall Pressure. Zero pressure is the reference for other pressures measured with the technique.

Figure 19:
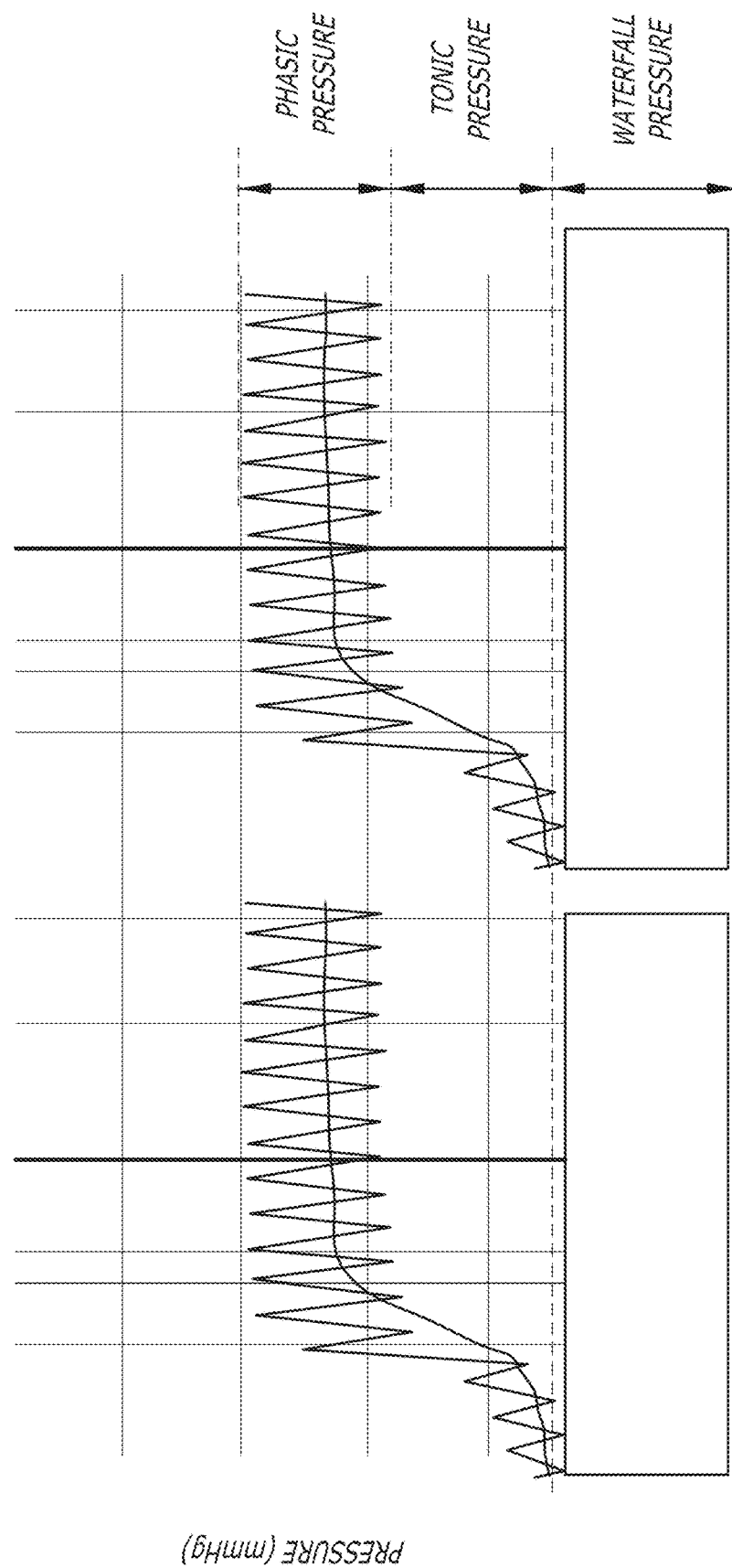
FIG. 19 is a chart showing phasic resistance, tonic resistance and waterfall pressure.

FIG. 19 is a graph of a pressure recording distal to an inflated coronary artery balloon of the invention, with a controlled fluid flow infusion. The waveform readily shows the waterfall pressure, and an induced waveform having both tonic and phasic components. The tonic resistance is an offset of (DC pressure component) modulated by a phasic wave (AC pressure component). These pressure waveforms of the invention are key entities to assessing the microvasculature, and are directly related to microvascular resistance by the same relationship above, $P=Q \times R$. The tonic component measures basal microvascular tone, while the phasic component measures dynamic resistance that results from cyclical myocardial contraction. During systole, myocardial contraction collapses the microvasculature and raises resistance. During diastole, the myocardium relaxes, opening the microvasculature and the microvasculature decreases. These entities are very valuable to assessing microvascular obstruction and heart function, especially during an acute heart attack. This diagram shows measured pressure waveform decompensation distal to the balloon occlusion.

Figure 20:
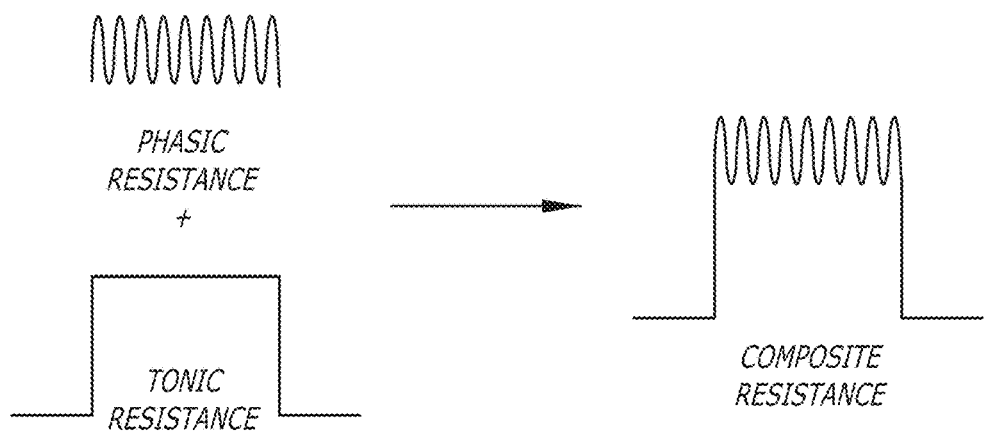
FIG. 20 is a graphic explaining composite resistance.

FIG. 20 depicts the addition of the phasic resistance and tonic resistance components into a composite tonic and phasic waveform. The measured pressure waveform comprises phasic pressure, which is added to tonic pressure resulting in a composite phasic-tonic pressure waveform. The proximal balloon occlusion in combination with fixed, pump driven flow infusion rate yield the measured pressures which in sum comprise a unique method to yield total microvascular resistance, phasic microvascular resistance and tonic microvascular resistance. Each component, tonic and phasic, are independent of one another and are hence provide very valuable insights into heart muscle and its microvascular blood supply not only during heart attack but also several other microvascular and heart muscle disease states.

Figure 21A:
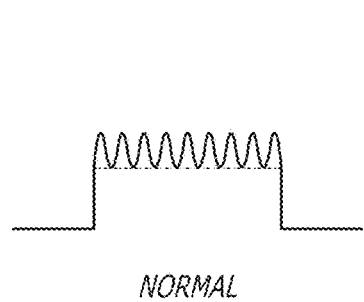
FIGS. 21a-d are graphics used to explain effects of the methods of the invention.
Figure 21B:
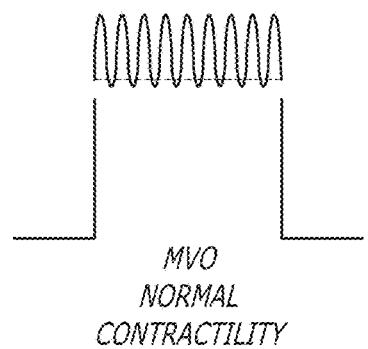
Figure 21C:
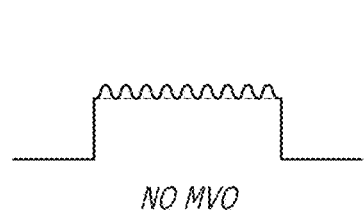
Figure 21D:
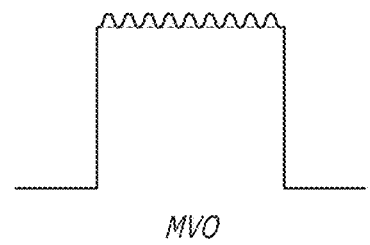

FIGS. 21a-d show examples of diagnostic methods of the invention. In a variety of disease states heart muscle and microvasculature can each independently be normal or abnormal. Controlled flow infusion in a heart with Normal flow/Normal contractility is shown in FIG. 21a. The remaining graphs show increases in infusion pressure and microvascular resistance following a balloon occlusion per an embodiment of a method of the invention; others respectively show waveforms from hearts with MVO and normal contractility/contraction (FIG. 21b), No MVO and normal contractility (FIG. 21c), Low contractility and no MVO (FIG. 21d). The invention rapidly simplifies the complex interactions of MVO and contractility, especially during STEMI, not possible with any other method.

Figure 22:
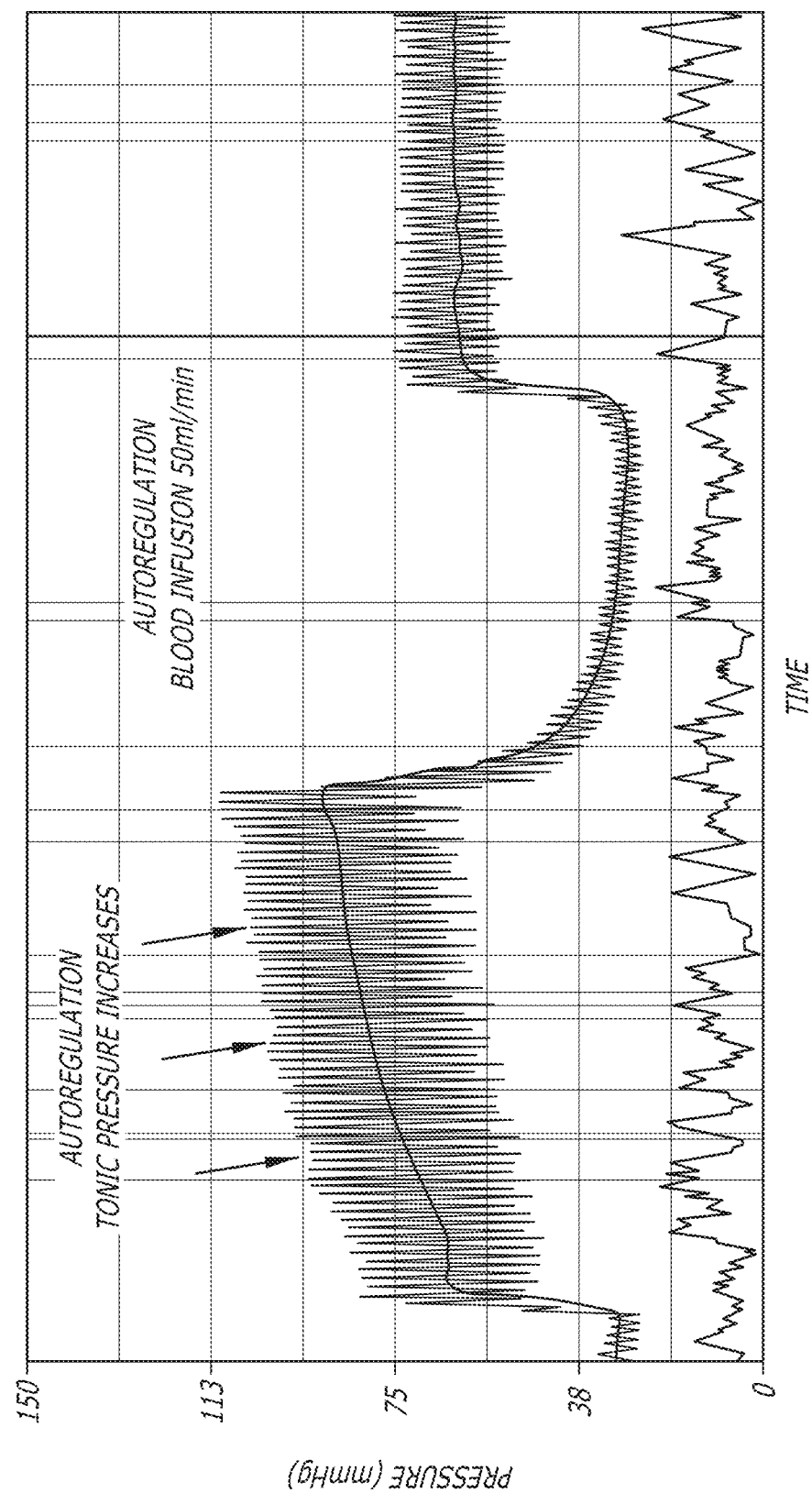
FIG. 22 is a graph of blood pressure over time, showing an effect of an application of an embodiment of a method of the invention.

FIG. 22 shows a measurement of autoregulation capability in a heart, facilitated by the controlled flow infusion invention. The figure shows controlled, whole blood infusion distal to a balloon occlusion of 50 ml/minute. Microvascular based autoregulation physiologic functions. Organ blood flow is typically auto regulated over a wide range of blood pressures. This figure shows progressive back pressure increase (in tonic pressure) over the controlled flow infusion, demonstrating the microvasculature contracting and raising microvascular resistance as it (unsuccessfully) attempts flow limitation. Because the flow is supplied by the external, powered pump, flow cannot be limited by the natural autoregulatory mechanism, and pressure increases in direct proportion to the increasing microvascular resistance. This information is available in real time by the invention methods.

Figure 23:
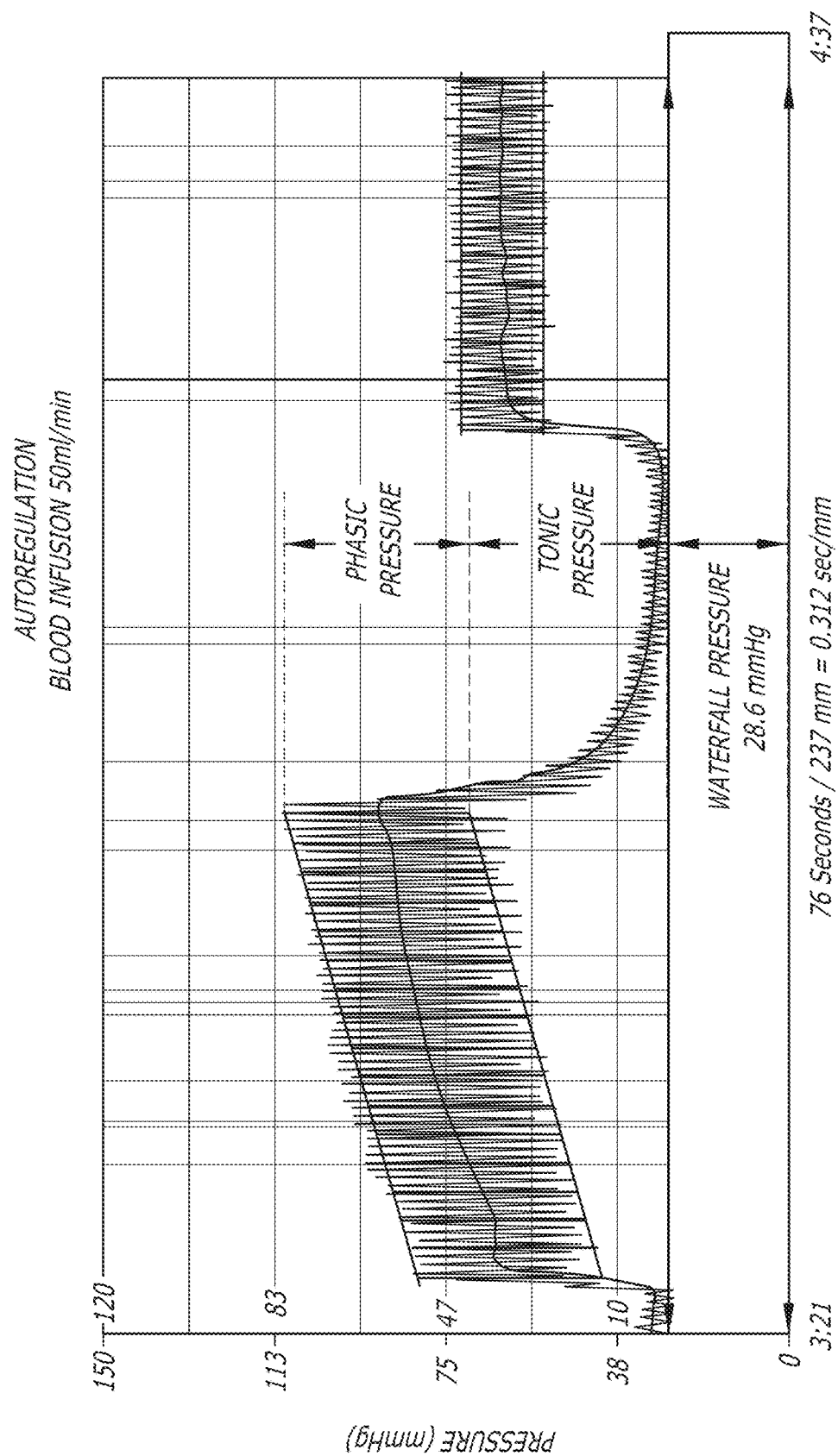
FIG. 23 is a graph of blood pressure over time, showing an effect of an application of an embodiment of a method of the invention.

FIG. 23 is an example of a method of the invention, being performed on a living and beating heart, to quantify absolute and relative microvascular resistance changes due to autoregulation. The figure shows tonic pressure increase linearly with time, roughly +1 mmHg/second. Phasic resistance does not change (the peak pressure lines remain parallel), illustrating tonic-phasic resistance independence. Myocardial contractility in this heart remains constant as evidenced by the phasic resistance being constant.

Figure 25:
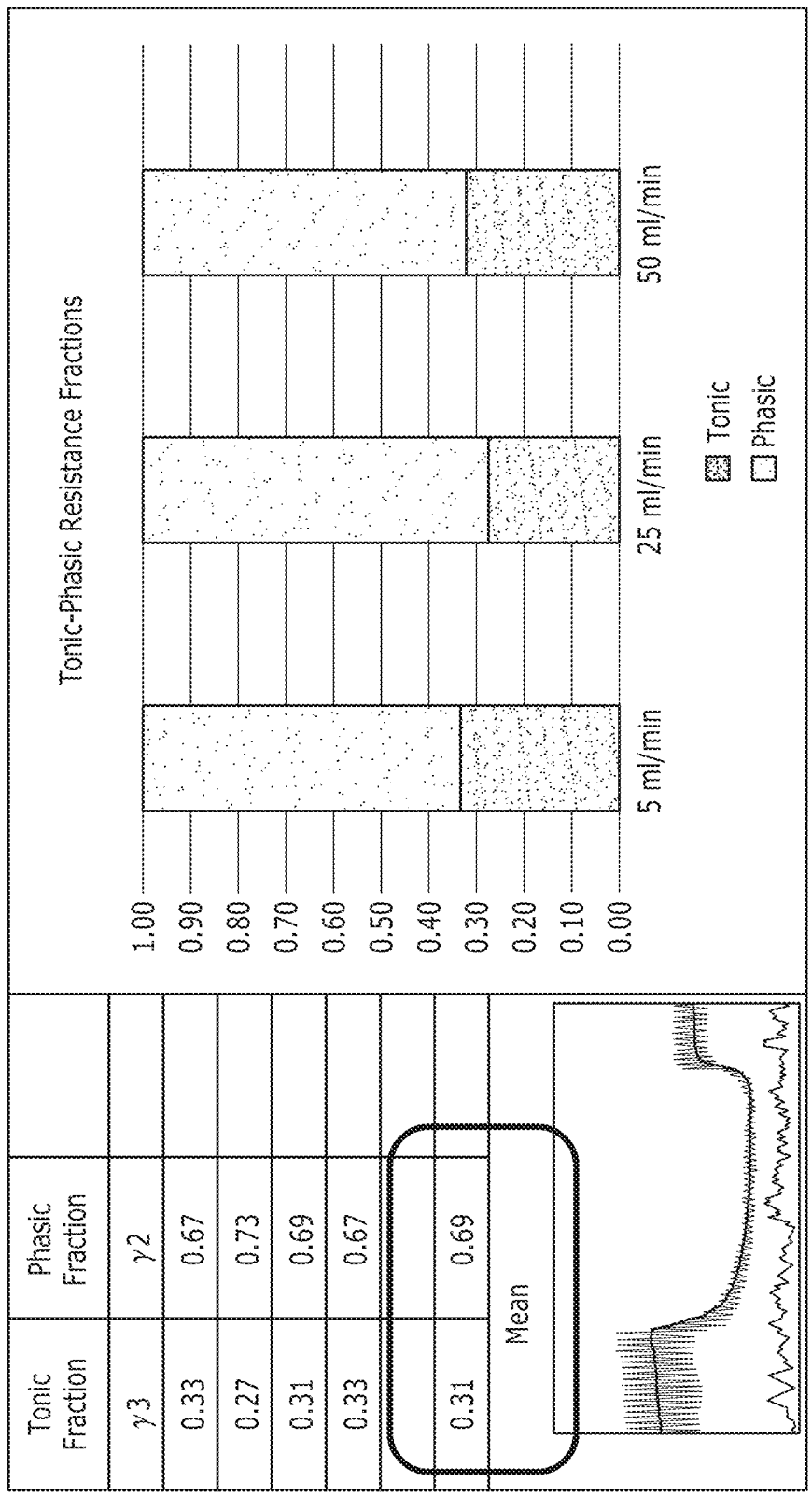
FIG. 25 is a graphic showing data obtained from an experimental study using an embodiment of a method of the invention; and, FIG. 26 is a graphic showing microvascular resistance at various tonic, phasic and total flow rates.

FIG. 25 shows data from an experimental study using the methods of the invention. The right side of the figure shows graphs depicting relative amplitude of phasic and tonic resistance in this beating heart, across 3 infused flow rates. The left side of the figure shows numerical values.

Figure 26:
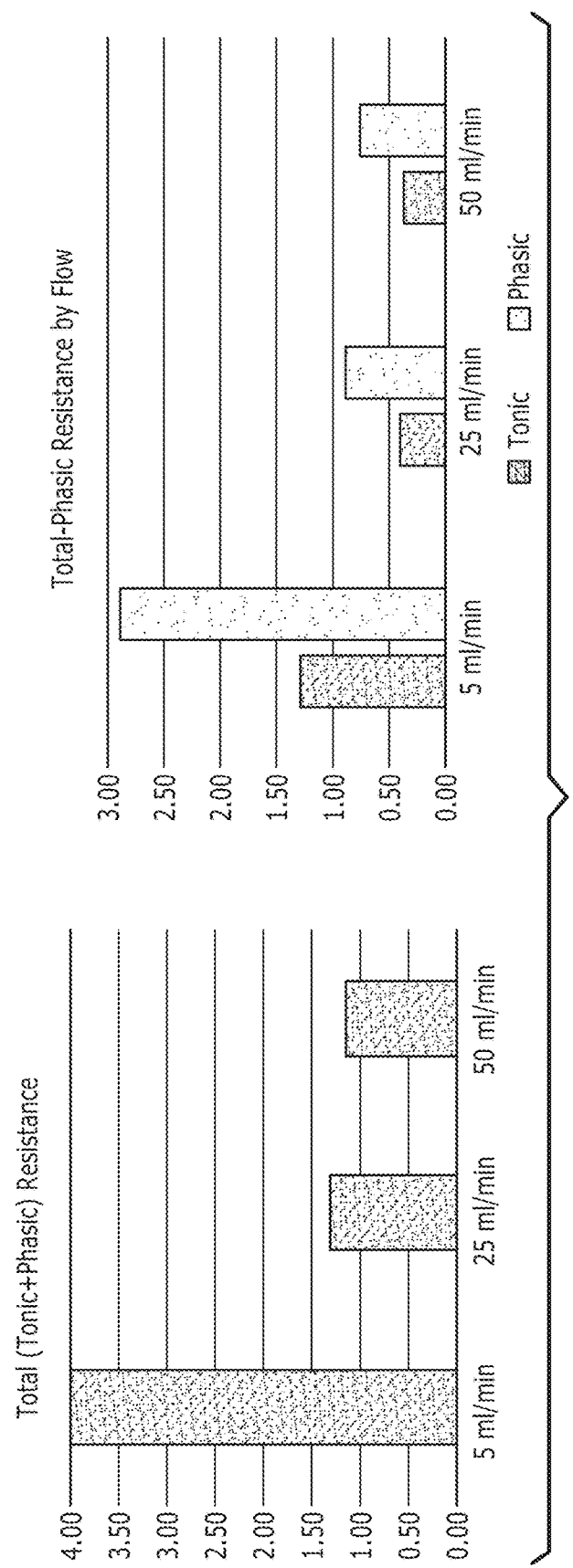

FIG. 26 shows microvascular resistance is constant at high flow rates, but rises substantially at low flow rate (5 ml/min). This is due to the Waterfall Effect, where microvessels close at low interstitial myocardial pressure.

While the invention is described in particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for treating Microvascular Obstruction (MVO) comprising:
   navigating a catheter into a myocardial vessel supplying blood to a patient's myocardium with MVO;
   blocking antegrade and retrograde blood flow within the vessel around said catheter using a balloon;
   measuring a fluid pressure of the myocardial vessel occurring distal of the balloon;
   introducing infusate through a lumen of said catheter at predetermined flow rates;
   allowing natural myocardial contraction and compression of microvasculature to pump the infusate antegrade into occluded myocardial vessels and to promote mixing of the infusate with obstructing matter causing MVO;
   collecting data pertinent to pressure parameters in the myocardial vessel;
   analyzing the collected data to determine a change resulting from said treating the MVO.

2. The method of claim 1 further comprising measuring temperature of the fluid in the myocardial vessel.

3. The method of claim 2 further comprising collecting data pertinent to temperature parameters in the myocardial vessel.

4. The method of claim 1 wherein introducing infusate through the lumen of the catheter comprises repeating an inject-stop-hold pattern until total elapsed occlusion time nears that of physiologic myocardial or organ injury due to ischemia.

5. The method of claim 1 wherein introducing infusate through the lumen of the catheter comprises introducing infusate through an arterial or venous lumen at at least one predetermined flow rate.

6. The method of claim 5 further comprising varying said predetermined flow rate to match a waveform.

7. The method of claim 6 wherein said waveform is selected from the group steady, square, triangle, sine, step-function, and custom time dependence.

8. The method of claim 1 wherein analyzing the collected data comprises deriving a value Tau, where Tau is derived as a mono-exponential fit $P(t)=P_0^{-t/Tau}$.

9. The method of claim 8 further comprising determining a waterfall pressure, wherein said waterfall pressure is defined as the asymptotic value of the monoexponential Tau fit.

10. The method of claim 9 further comprising using said waterfall pressure as a guide for infusion pressure and flow.

11. The method of claim 1 wherein analyzing the collected data comprises quantifying the flow rate through the myocardium.

12. The method of claim 1 wherein the step of blocking antegrade and retrograde blood flow within the vessel around a said catheter using a balloon comprises blocking the antegrade and retrograde blood flow within the vessel around said catheter using at least a first balloon and a second balloon spaced apart from the first balloon.

13. The method of claim 12 further comprising measuring pressure between the first balloon and the second balloons.

14. A method of reestablishing blood flow through occluded microvessels comprising:
   navigating a catheter into a vessel supplying blood to the occluded vessels;
   blocking antegrade and retrograde blood flow around a distal end of said catheter;
   monitoring at least one of a pressure inside the catheter, and a pressure outside a distal end of the catheter;
   pumping infusate through a lumen of said catheter in a patterned response having a pattern that is selected based on at least one monitored pressure;
   preventing retrograde flow of the infusate around the catheter such that natural cardiac contractions at least partially aid in pumping the infusate antegrade into the occluded vessels;
   altering the pattern as the at least one monitored flow, pressure or resistance change;

analyzing data collected during the monitoring step to determine whether and to what extent blood flow has been reestablished.

15. The method of claim 14 wherein said patterned response comprises a repeating inject-stop-hold pattern.

16. The method of claim 15 wherein the inject portion of the inject-stop-hold pattern comprises injecting at defined rates.

17. The method of claim 16 wherein the defined rates vary over time according to said monitored pressure.

18. The method of claim 14 wherein said patterned response matches a waveform having amplitudes and phases derived from said at least one monitored pressure.

19. The method of claim 14 wherein analyzing data collected comprises deriving a value Tau, where Tau is derived as a mono-exponential fit of the equation $$P(t)=P_0 e^{-t/Tau}.$$

20. The method of claim 19 wherein analyzing data collected comprises determining a waterfall pressure, wherein said waterfall pressure is defined as the asymptote of the monoexponential fit.

21. The method of claim 20 further comprising using said waterfall pressure as a guide for infusion pressure of therapeutic or diagnostic agents.

22. The method of claim 14 wherein analyzing data collected comprises quantifying the microvascular state and flow rate through the myocardium.

23. The method of claim 14 wherein analyzing data collected comprises determining an autoregulatory status of an organ's microvascular function.

\* \* \* \* \*